(12) United States Patent
Larson et al.

(10) Patent No.: US 10,827,959 B2
(45) Date of Patent: Nov. 10, 2020

(54) SENSOR SET

(71) Applicant: Medtronic MiniMed, Inc., Northridge, CA (US)

(72) Inventors: Eric Allan Larson, Simi Valley, CA (US); Ashley N. Sullivan, West Hollywood, CA (US); Chase A. Thompson, Sherman Oaks, CA (US); David C. Antonio, Pasadena, CA (US); Jose J. Ruelas, San Fernando, CA (US); Megan E. Little, Pasadena, CA (US); Joseph P. Brinson, Canyon Country, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 531 days.

(21) Appl. No.: 15/347,521

(22) Filed: Nov. 9, 2016

(65) Prior Publication Data
US 2017/0127982 A1 May 11, 2017

Related U.S. Application Data

(63) Continuation-in-part of application No. 14/938,458, filed on Nov. 11, 2015, now abandoned.
(Continued)

(51) Int. Cl.
*A61B 5/1477* (2006.01)
*H01R 12/77* (2011.01)
(Continued)

(52) U.S. Cl.
CPC .......... *A61B 5/1477* (2013.01); *A61B 5/0022* (2013.01); *A61B 5/1473* (2013.01);
(Continued)

(58) Field of Classification Search
USPC ........................................................ 600/347
See application file for complete search history.

(56) References Cited

U.S. PATENT DOCUMENTS

| 4,755,173 | A | | 7/1988 | Konopka et al. |
| 5,108,311 | A | * | 4/1992 | Nakazawa ........... H01R 13/629 439/607.32 |

(Continued)

FOREIGN PATENT DOCUMENTS

| EP | 1032087 A1 | 8/2000 |
| JP | 2002-537634 | 11/2012 |
| WO | 2013111915 A1 | 8/2013 |

OTHER PUBLICATIONS

PCT International Search Report and Written Opinion for Application No. PCT/US2016/061363 dated Jan. 19, 2017.

*Primary Examiner* — Christian Jang
*Assistant Examiner* — Mitchell E Alter
(74) *Attorney, Agent, or Firm* — Medtronic Minimed, Inc.

(57) ABSTRACT

A sensor set is provided for sensing of a body characteristic, such as glucose. The sensor set includes a mounting base for the sensor and a connector to connect to the mounting base and has an improved structure for connecting the mounting base to the connector. The connector may contain sensor electronics for wired or wireless communication to an external monitor or display. The mounting base includes latch arms and the connector adapted to fit and lock into latch recesses on the connector and includes anti-rotation arms adapted to fit into anti-rotation arm recesses on the connector.

18 Claims, 22 Drawing Sheets

Related U.S. Application Data

(60) Provisional application No. 62/400,987, filed on Sep. 28, 2016.

(51) Int. Cl.

| | | |
|---|---|---|
| *H01R 13/645* | (2006.01) | |
| *A61B 5/1473* | (2006.01) | |
| *A61B 5/00* | (2006.01) | |
| *A61B 5/145* | (2006.01) | |
| *A61B 5/1495* | (2006.01) | |
| *H01R 13/627* | (2006.01) | |

(52) U.S. Cl.
CPC ........ *A61B 5/1495* (2013.01); *A61B 5/14532* (2013.01); *A61B 5/6833* (2013.01); *H01R 12/778* (2013.01); *H01R 13/6456* (2013.01); *A61B 5/002* (2013.01); *A61B 5/6849* (2013.01); *H01R 13/6273* (2013.01); *H01R 2201/12* (2013.01)

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,885,088 A * | 3/1999 | Brennan ................ H01R 13/64 439/378 |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2002/0053523 A1* | 5/2002 | Liamos ............ G01N 27/3272 205/787 |
| 2002/0072275 A1* | 6/2002 | Arai .................... H01R 13/6456 439/680 |
| 2006/0001550 A1* | 1/2006 | Mann .................... A61B 5/0002 340/870.07 |
| 2007/0123819 A1 | 5/2007 | Mernoe et al. |
| 2008/0064944 A1* | 3/2008 | Vanantwerp ....... A61B 5/14532 600/373 |
| 2010/0105226 A1* | 4/2010 | Gong ................ H01R 13/7031 439/135 |
| 2010/0160861 A1 | 6/2010 | Causey, III et al. |
| 2013/0313130 A1* | 11/2013 | Little ................ A61B 5/14865 205/792 |

* cited by examiner

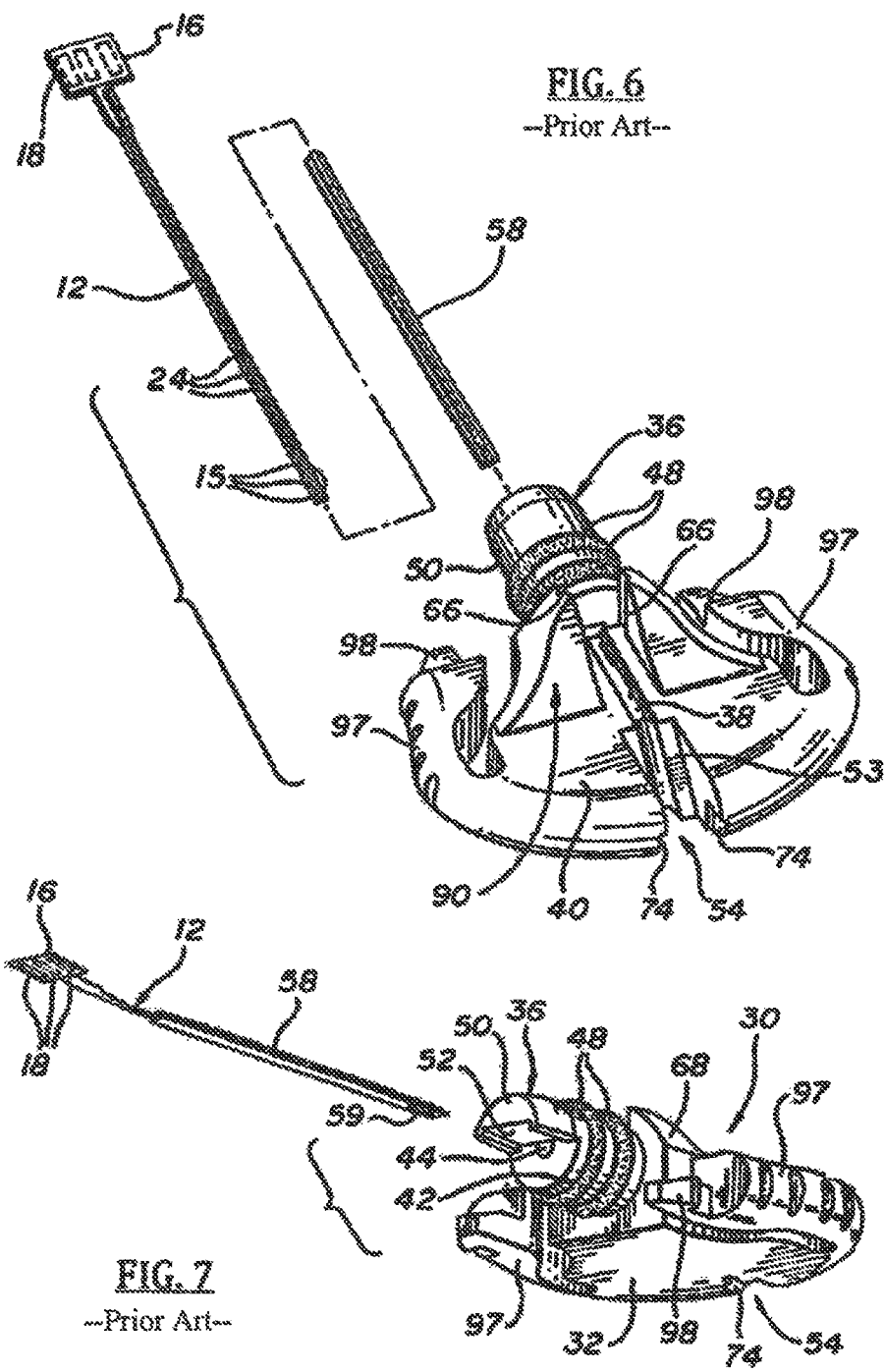

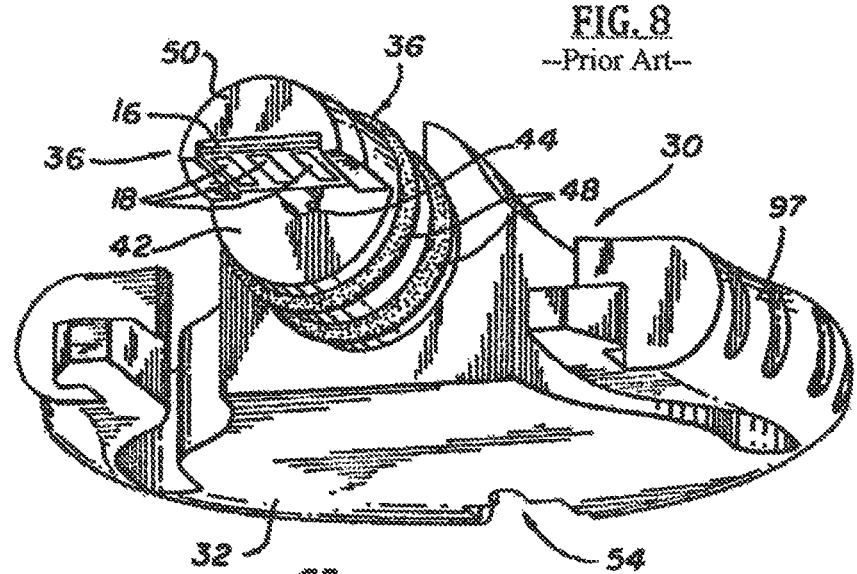
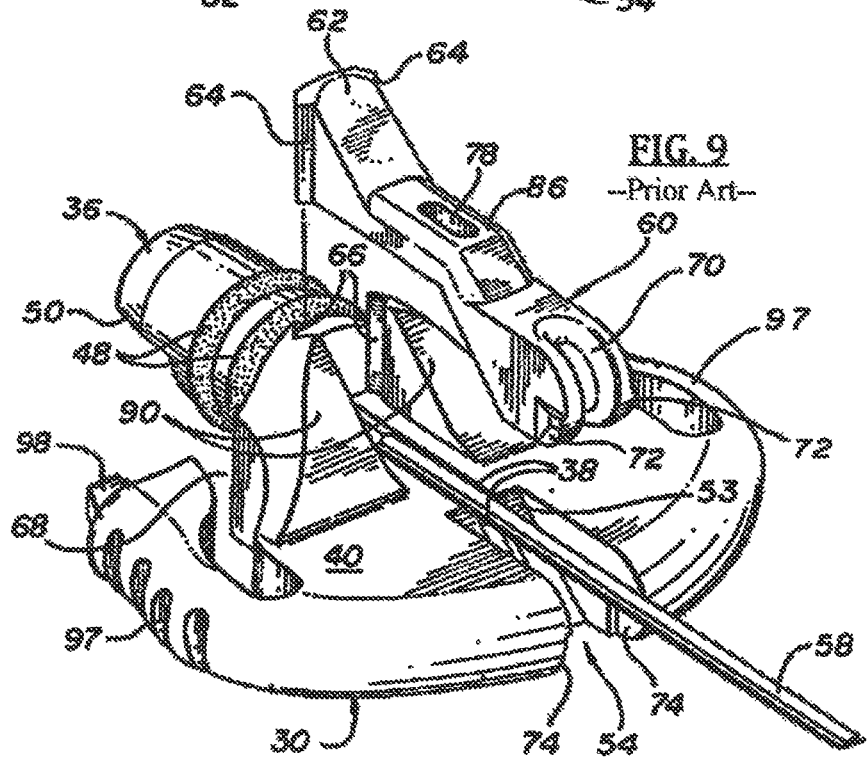

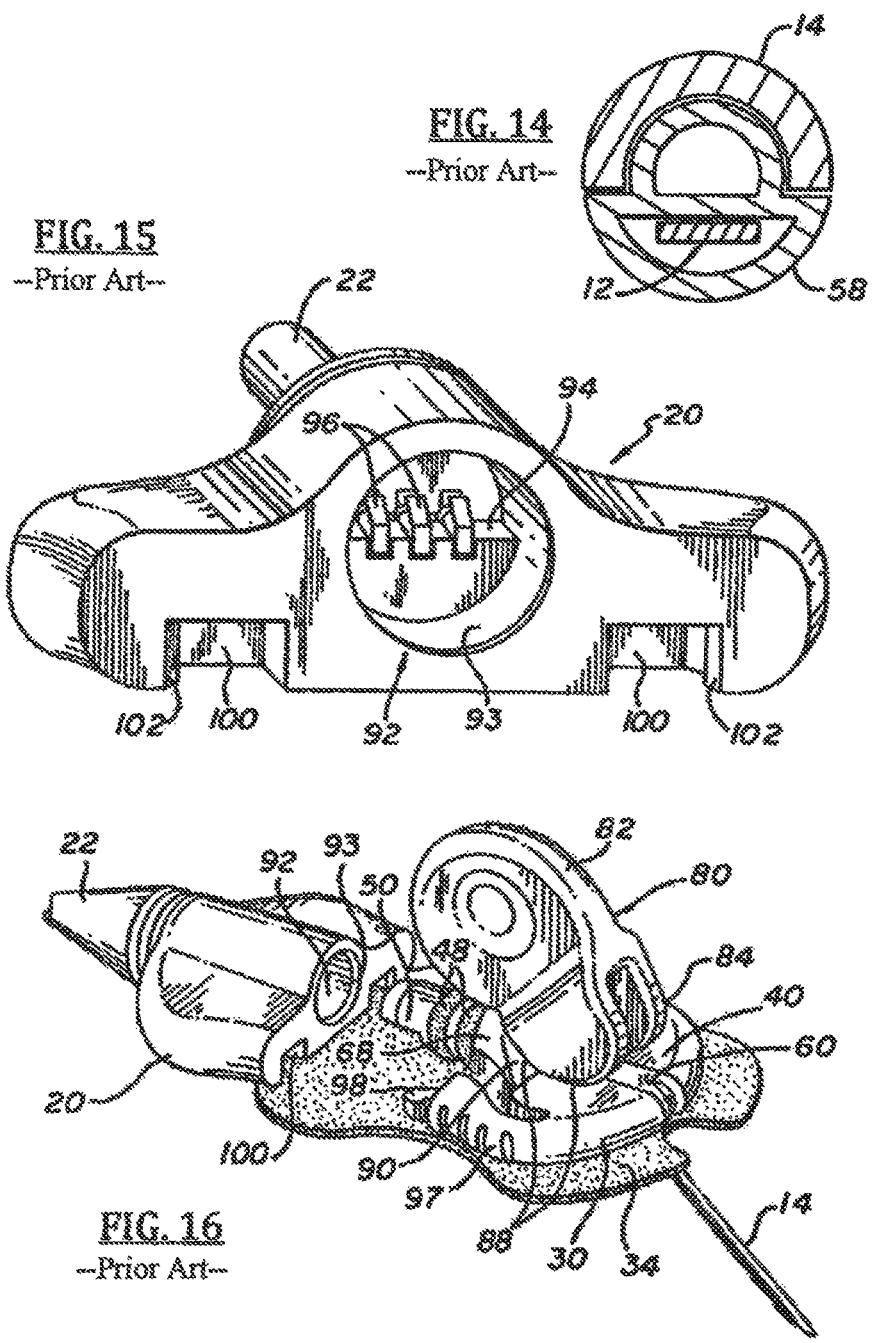

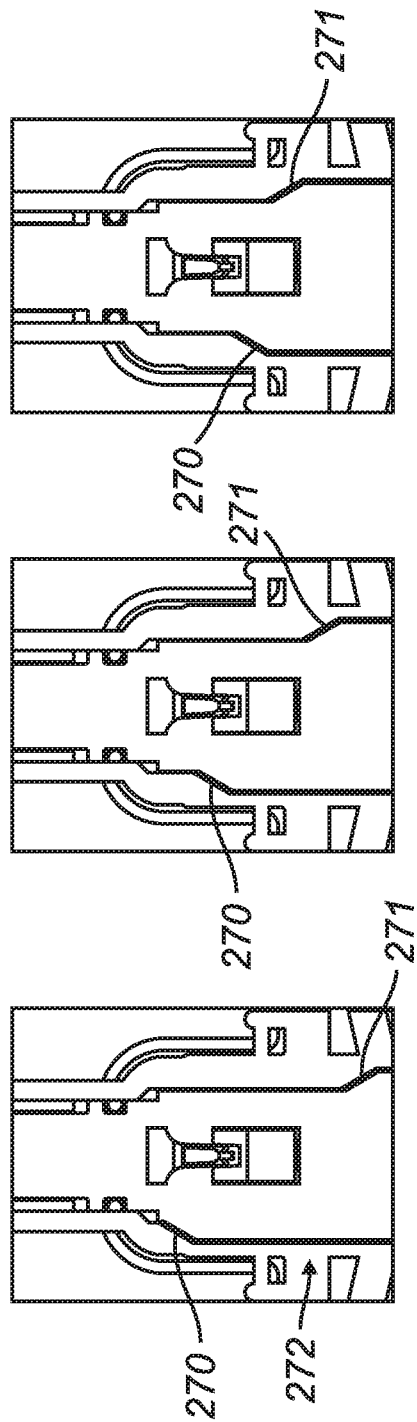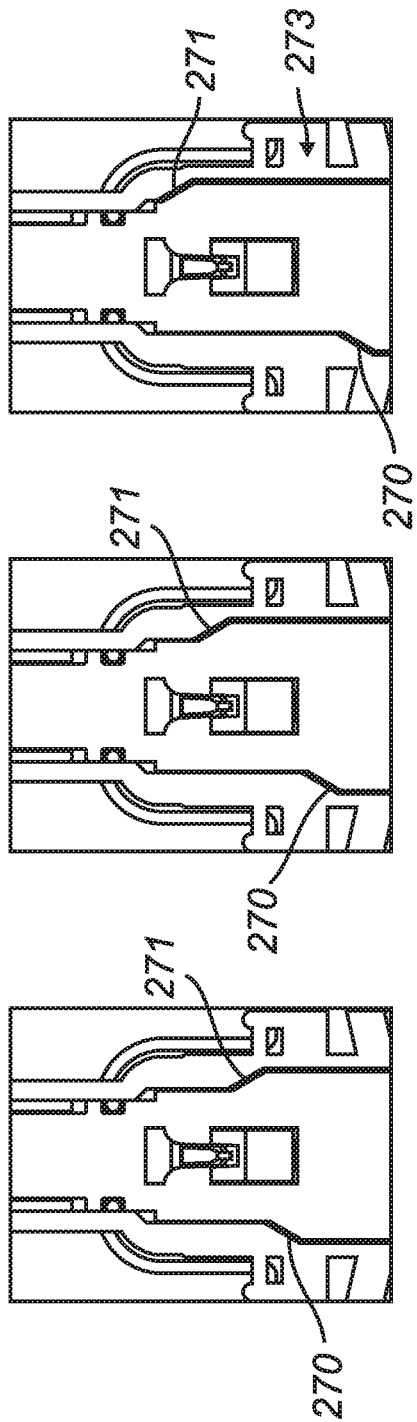

SENSOR SET

CROSS-REFERENCE TO RELATED APPLICATIONS

This patent application is a continuation-in-part application of U.S. patent application Ser. No. 14/938,458, filed on Nov. 11, 2015, the entirety of which is herein incorporated by reference. Also, the present disclosure claims the benefit of and priority to U.S. Provisional Application No. 62/400,987, filed on Sep. 28, 2016, the entirety of which is herein incorporated by reference.

BACKGROUND OF THE INVENTION

Field of the Invention

The present invention generally relates to connection arrangements particularly for use in a sensor set and insertion set for monitoring a body characteristic of the body, such as glucose. More particularly, the present invention relates to connectors for coupling components of a sensor set including a mounting base or test plug with a connector.

Description of the Related Art

In recent years, a variety of electrochemical sensors have been developed for a range of applications, including medical applications for detecting and/or quantifying specific agents in a patient's blood and other body fluids. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for subcutaneous placement in direct contact with patient blood or the like, and exposed conductive contact pads at an externally located proximal end for convenient electrical connection with a suitable monitoring device. Such thin film sensors hold significant promise in patient monitoring applications, but unfortunately have been difficult to place transcutaneously with the sensor electrodes in direct contact with patient blood or other body fluid. Improved thin film sensors and related insertion sets are described in commonly assigned U.S. Pat. Nos. 5,390,671; 5,391,250; 5,482,473; 5,299,571; 5,586,553 and 5,568,806, which are incorporated by reference herein.

US 2008/0064944 (U.S. Pat. No. 7,660,615), which is herein incorporated by reference, discloses a known insertion set coupling. It includes a mounting base for a subcutaneously placed foil sensor. The mounting base itself has a flat underside provided with a pressure sensitive adhesive allowing the mounting base to be stuck on the surface of a patient's skin as a stick-on patch. The coupling is provided between the mounting base and a cable connector by means of a cylindrical connector fitting extending from the mounting base. This fits within a corresponding socket of the cable connector. "O" rings around the base of the cylindrical connector fitting provide a seal. The end of the connector fitting is partially cut away leaving a "D" cross section and producing a flat surface parallel to the axis of the connector fitting. A contact-bearing head of the sensor foil is supported on this flat surface. When the connector fitting and the socket engage, spring contacts within the socket touch and connect to the contact pads the sensor foil.

Currently, there are sensor sets that include a mounting base, for placement on the patient's skin, which can be coupled to a connector with suitable sensor electronics (wired or wireless). Because the mounting base may be sold separately, it is possible to attach incompatible components together, which can compromise the sensor data. In addition, the structure of the current sensors allows for limited number of contact pads, and respective sensor electrodes.

SUMMARY OF THE INVENTION

In aspects, a sensor set for sensing a characteristic of a patient is provided, the sensor set comprising a sensor having a distal segment thereon at a distal end for generating at least one electrical signal representative of a characteristic, such as blood glucose, of a patient, the sensor including at least two contact pads at a proximal end, wherein each of the at least two contact pads are coupled to the distal segment to receive the electrical signals therefrom; a mounting base operable for mounting onto a patient's skin, the mounting base including a connector fitting generally at a rear end of the mounting base, wherein the connector fitting includes a tubular element having a central bore formed therein for pass through reception of a portion of the sensor, a connector operable to couple to the mounting base, wherein the connector includes a tubular recess sized to receive the connector fitting of the mounting base and at least two connector contacts that are operable to be electrically coupled to the at least two contact pads of the sensor when the mounting base is coupled to the connector, wherein the connector fitting includes a key formed at one end, wherein the proximal end of the sensor folds around the key such that at least one of the at least two contact pads is on a first side of the key and at least one other of the at least two contact pads is on a second side of the key. The distal segment may include electrodes for measuring blood glucose which may for example be configured in a potentiostat. The coupling between the distal segment and the contact pad may include electronics to power the sensor and/or process the signals. The sensor may be a foil with conductor tracks and electronic components produced according to known thin film technology.

A test plug may be included as part of the sensor set in addition to the mounting base. The test plug may be sold as part of the sensor set or separately. It is also possible to sell components of the sensor set, such as the mounting base or the connector, without the other components.

The at least two connector contacts of the connector may be compressible pins. In still further embodiments, the compressible pins compress into the first side of the key and the second side of the key when the mounting base is coupled to the connector.

It is also envisioned that a test plug may be included, which in construction is the same as the embodiment discussed above, but in which the sensor is replaced by a flexible circuit foil having the contact pads and, in place of the coupling to a distal segment, has circuits to generate test signals.

The sensor or test plug circuit foil may include a shorting path allowing for a shorted reference electrode and counter electrode. Alternatively, or in addition, the sensor or test plug circuit may include a resistor.

The key may be substantially oval or rectangular in shape. In embodiments, the first side of the key is substantially flat. The second side of the key may also be substantially flat or it may include a substantially flat end portion and a step portion. One or both sides of the key may include seats or flats to receive the proximal end of the sensor. In embodiments, the key includes at least one prong adapted to fit into a prong recess formed in the mounting base. The first side of the key is substantially flat.

The mounting base may include at least one arm generally adjacent to the tubular element of the connector fitting, wherein the at least one arm is formed to fit into at least one corresponding arm recess formed in the connector when the connector is connected to the mounting base.

The connector fitting may include a first side rail formed on a first side of the connector fitting and a second side rail formed on a second side of the side rail, wherein the first side rail and second side rail are operable to slide into a first slot formed in the mounting base tubular recess and a second slot formed in the connector tubular recess when the connector is connected to the mounting base.

The connector may include sensor electronics, for example including a wireless transmitter operable to transmit signals from the mounting base. The at least two sensor electrodes may be operable to generate at least two electrical signals representative of the characteristic and the at least two connector contacts may be operable to receive the at least two electrical signals. These electrical signals may be transmitted via wireless transmitter or transmitted over wire.

The mounting base and the connector may have releasably interengageable snap fit latch members operable to lock the mounting base to the connector.

It may be helpful to envision the key as being an extension of the tubular element of the connector fitting from which sectors or segments have been cut-away. Thus is the case of a "D" section key for example as shown in US 2008/0064944 the cut-away portion is the lower half of the tubular element. This does not imply that the key is actually manufactured by starting with a cylinder and removing material, but this is useful to define the finished shape.

According to a second aspect, a connector system comprises: a connector foil having contact pads thereon at an end portion; a cylindrical connector fitting having a cylindrical element with a key formed at its distal end, said key being defined by cut-away portions of the cylindrical element to produce two flat surfaces each parallel to the axis of the cylindrical element, which flat surfaces face away from one another; wherein the end portion of the connector foil lies against a first one of said flat surfaces with the contact pads facing away from the first flat surface; a socket unit with a tubular recess sized to accommodate the cylindrical element and having contacts positioned to engage the contact pads of the connector foil, the socket unit having a structure occupying the space vacated by said cut-away portions. The connector foil may wrap around the end of the key so as to lie on both flat surfaces with contact pads facing away from the flat surfaces. As an alternative to the foil wrapping around the end of the key, it may lie only against one side of the key and the structure occupying the space vacated by said cut-away portions may comprise spring contacts on one side of the key and a projection on the inside of the tubular recess on the other side of the key. The first flat surface may lie on a diameter of the cylindrical element. Thus, on each side of the key there are either contacts or a projection being part of the socket. This helps stabilize the connector system, leading to a more reliable connection.

It is also envisioned that the end of the key may have a predetermined profile, and an inner end of the tubular recess may have a complementary inter-engaging profile. This can be useful to prevent engagement of non-compatible components.

Further stability can be provided by the use of side walls on the flat surfaces of the key to protect the connector foil. Preferably the side walls are at least as high as the foil is thick, the foil thereby resting in a shallow cradle on the flat surface of the key. In arrangements under the first folds over the end of the key side walls may only be on the first surface.

According to a yet further aspect there is provided a sensor set for sensing a characteristic of a patient, the sensor set including the connector system of the above described aspect wherein the connector foil comprises a medical sensor having the contact pads at a proximal end and a sensing structure at a distal end and a medial section, wherein the tubular element is formed as part of a mounting base operable for mounting onto a patient's skin and has a central bore for pass through reception of the medial section of the medical sensor. In an alternative arrangement, there is provided a test plug including the above described connector system, wherein the connector foil comprises a test circuit to test equipment coupled to the socket unit when the plug unit and the socket unit are connected.

In another aspect, a sensor set is provided for sensing a characteristic of a patient, the sensor set comprising: a sensor having at least two sensor electrodes thereon at a distal end for generating at least one electrical signal representative of a characteristic of a patient, the sensor including at least two contact pads at a proximal end, wherein each of the at least two contact pads are conductively coupled to at least one of the at least two sensor electrodes; a mounting base adapted to mount onto a patient's skin and to connect the sensor to sensor electronics, the mounting base including a connector fitting generally at a rear end of the mounting base, wherein the connector fitting includes a cylindrical element having a central bore formed therein for pass through reception of a portion of the sensor, a connector adapted to couple to the mounting base, wherein the connector includes a cylindrical recess sized to receive the connector fitting of the mounting base and at least two connector contacts that are adapted to be electrically coupled to the at least two contact pads of the sensor when the mounting base is coupled to the connector, wherein the mounting base includes one or more latch arms and the connector includes one or more latch recesses, and wherein the one or more latch arms are adapted to fit and lock into the one or more latch recesses when the mounting base is coupled to the connector, and wherein the mounting base further includes one or more anti-rotation arms and the connector includes one more anti-rotation arm recesses, wherein the one or more anti-rotation arms are adapted to fit into the one or more anti-rotation arm recesses when the mounting base is coupled to the connector. The anti-rotation arms may be wider than their height. The one or more latch recesses are the same as the one or more anti-rotation arm recesses, such that the one or more latches fit into the same recesses as the one or more anti-rotation arms.

The mounting base may further include one or more lockout columns extending in the same direction as the one or more latch recesses and the connector includes one or more lockout pockets adapted to fit the lockout columns, wherein when the mounting base is coupled to the connector.

A test plug may be adapted to connect to the connector, with similar connections. For example, the test plug may include one or more test plug latch arms adapted to fit and lock into the one or more latch recesses of the connector when the test plug is coupled to the connector, and the test plug may further include one or more test plug anti-rotation arms adapted to fit into the one or more anti-rotation recesses of the connector when the test plug is coupled to the connector. The test plug may include one or more anti-rotation arm extensions between a central section of the test plug and the anti-rotation arms, wherein the anti-rotation arm extensions slope from the top of the central section to the anti-rotation arm extensions. The test plug may also include one or more test plug lockout columns extending in the same direction as the one or more test plug latch recesses adapted to fit into the lockout pockets of the connector when the test plug is coupled to the connector.

The connector fitting may include a key formed at one end, where the proximal end of the sensor folds around the key such that at least one of the at least two contact pads is on a first side of the key and at least one other of the at least two contact pads is on a second side of the key. The key may include at least one prong adapted to fit into a prong recess formed in the mounting base. The first side of the key may be substantially flat. The first side of the key and the second side of the key each include seats to receive the proximal end of the sensor.

The at least two connector contacts of the connector may be compressible pins. The compressible pins compress into the first side of the key and the second side of the key when the mounting base is coupled to the connector.

The sensor may include a shorting path allowing for a shorted reference electrode and counter electrode. The sensor may include a resistor. The connector may include a wireless transmitter adapted to transmit signals from the mounting base. The characteristic of the patient is envisaged to be blood glucose. The at least two sensor electrodes are adapted to generate at least two electrical signals representative of the characteristic and the at least two connector contacts are adapted to receive the at least two electrical signals.

In yet another aspect, a mounting base for a sensor includes: a connector fitting generally at a rear end of the mounting base, where the connector fitting includes a cylindrical element having a central bore formed therein for pass through reception of a portion of a sensor, wherein the sensor has at least two sensor electrodes thereon at a distal end for generating at least one electrical signal representative of a characteristic of a patient, the sensor including at least two contact pads at a proximal end, where each of the at least two contact pads are conductively coupled to at least one of the at least two sensor electrodes. The mounting base also includes one or more latch arms adapted to fit and lock into one or more latch recesses on a connector, wherein the connector is adapted to couple to the mounting base and to connect the sensor to sensor electronics and includes a cylindrical recess sized to receive the connector fitting of the mounting base and at least two connector contacts that are adapted to be electrically coupled to the at least two contact pads of the sensor when the mounting base is coupled to the connector. And the mounting base also includes one or more anti-rotation arms adapted to fit into one or more anti-rotation recesses on the connector when the mounting base is coupled to the connector. The anti-rotation arms may be wider than they are in height.

BRIEF DESCRIPTION OF THE DRAWINGS

For a more complete understanding of the present disclosure, reference is now made to the following figures, wherein like reference numbers refer to similar items throughout the figures:

FIG. 6 illustrates an expanded perspective view showing assembly of the mounting base components, including a sensor.

FIG. 7 illustrates an underside, expanded view of the mounting base, including sensor, shown in FIG. 6.

FIG. 8 illustrates an underside view of the mounting base shown in FIG. 6.

FIG. 9 illustrates another expanded view of a mounting base with retainer cap.

FIG. 14 illustrates a sectional view taken generally on the line 11-11 of FIG. 10.

FIG. 15 illustrates a front end perspective view of a connector in the form of a cable connector.

FIG. 16 illustrates an exploded perspective view of a connector in the form of a cable connector.

FIG. 27A-27F illustrates cut away views of various lockout connections between test plug or a mounting base and a connector.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual elements and functions are generally optional unless explicitly required, and the sequence of operations may vary. Portions and features of some embodiments may be included in, or substituted for, those of others. In particular, any structure described in respect to the coupling between a test plug and a connector applies also to the coupling between a corresponding mounting base and the connector.

Figure 1:
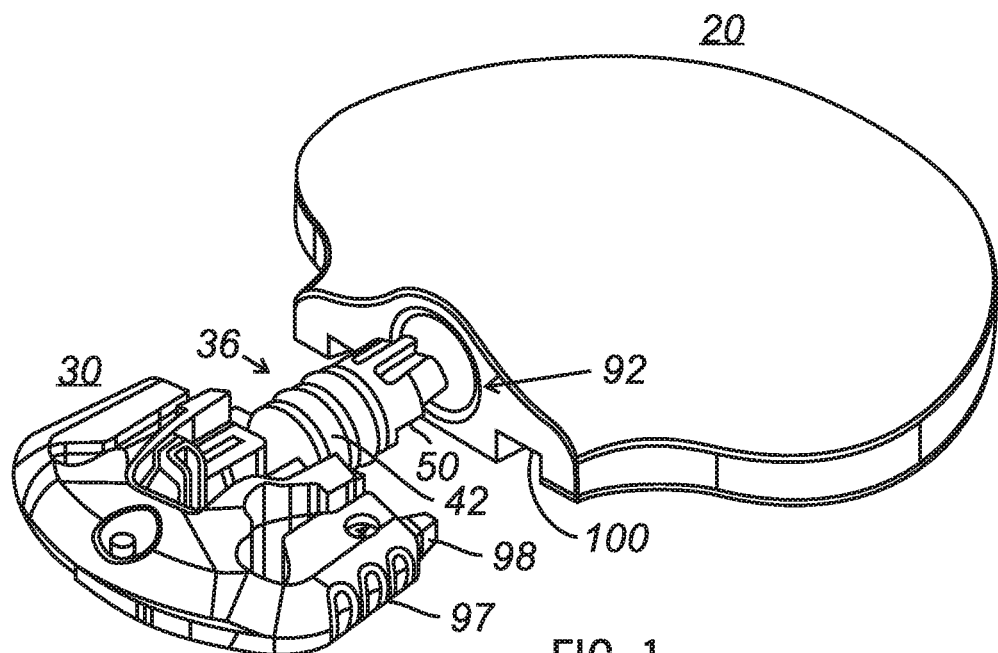
FIG. 1 illustrates a perspective view of a connector and a mounting base.

As shown in the exemplary drawings, an improved sensor set is provided for monitoring a body characteristic of the body. Also provided is an improved structure of the connections between the various components of the sensor set. One example body characteristic is the blood glucose level of the body. As shown in FIG. 1, an embodiment of a sensor set includes a sensor mounting base 30 and connector 20. The connector 20 shown in FIG. 1 includes wireless sensor electronics that have a sensor transmitter (not shown) inside the housing.

Further detail of the connector 20 is given below in the discussion of FIG. 3. The mounting base 30 illustrated in FIG. 1 serves as a mount for the foil of a thin film sensor, as shown best in FIGS. 6 and 7 below. The mounting base 30 consists of a housing with a flat underside optionally provided with a pressure sensitive adhesive (not shown) allowing the mounting base 30 to be stuck on the surface of a patient's skin as a stick-on patch. One edge of the mounting base 30 comprises a cylindrical connector fitting 36 having a cylindrical or tubular element 42 with an axial bore 44. The cylindrical or tubular element 42 has a cut-away tip defining a key 50 including a flat surface parallel to its axis. Exposed contact pads 18 on a proximal end on the sensor are supported by this flat surface. A medial section of the foil of the sensor passes foil through the bore 44 of the cylindrical or tubular element, out through its underside of the mounting base, connecting the contact pads 18 to sensing elements beneath the skin of the patient. For sensing glucose concentration the sensing elements could typically be the electrodes 15 of a potentiostat. The connection between the contact pads and the sensing elements optionally includes processing circuitry.

The sensor mounting base 30 couples to the connector 20 by means of the cylindrical connector fitting 36. The connector 20 has a socket 92 sized to slide-fit engage with the connector fitting 36 of the mounting base. The cylindrical or tubular element 42 is optionally provided with a pair of spaced apart "O" rings 48 resting in external grooves 46 in its surface to seal against corresponding surfaces on the inside of the socket 92 and form a moisture moister-proof coupling. On each side of the connector filling 36, the mounting base 30 has resilient latch arms 97 and latch tips 98, which can snap into and be retained within latch recesses 100 on the connector 20. When the mounting base 30 is coupled to the connector 20, the latch tips 98 lock into the latch recesses 100. They can be released by pressing on the latch arms 97 so that the connector 20 can be removed from the mounting base. A narrow, generally oval or rectangular shaped fitting key 50 is formed as a rearward extension of a cylindrical or tubular element adapted to slide into a socket fitting 92 of the connector 20.

As mentioned above, the foremost tip of the connector fitting 36 extending from the cylindrical or tubular element 42 comprises a key 50. The key 50 is essentially of a cylindrical shape, either parallel sided, or slightly tapered at an end portion. Out of the shape of this end portion has been removed sectors to leave two or more flat surfaces parallel to the axis of the tubular element. In the arrangement shown in FIG. 1 the key 50 has the whole of its lower half removed such as to form downward facing "D" section. A pair of sectors on the upper side of the "D" are removed to produce a pair of flat surfaces separated by a central ridge. This structure is in greater detail in FIG. 24. The pair of flat surfaces face in an opposite direction from the flat surface of the straight side of the "D" shape. A correspondingly shaped structure within the socket 92 of the connector 20 enables the connector fitting to be supported from two parallel sides, thereby improving stability. In the FIG. 1 arrangement, connection pads on the foil of the thin film sensor (not shown) supported by the mounting base rest against the surface forming in cross-section straight side of the "D". These connection pads engage with spring contacts inside the socket 92 of the connector 20. Facing in the other direction are the pair of flat surfaces, which do not carry contacts, but nonetheless engage with corresponding surfaces of a projection the socket 92 of the connector 20.

Figure 2:
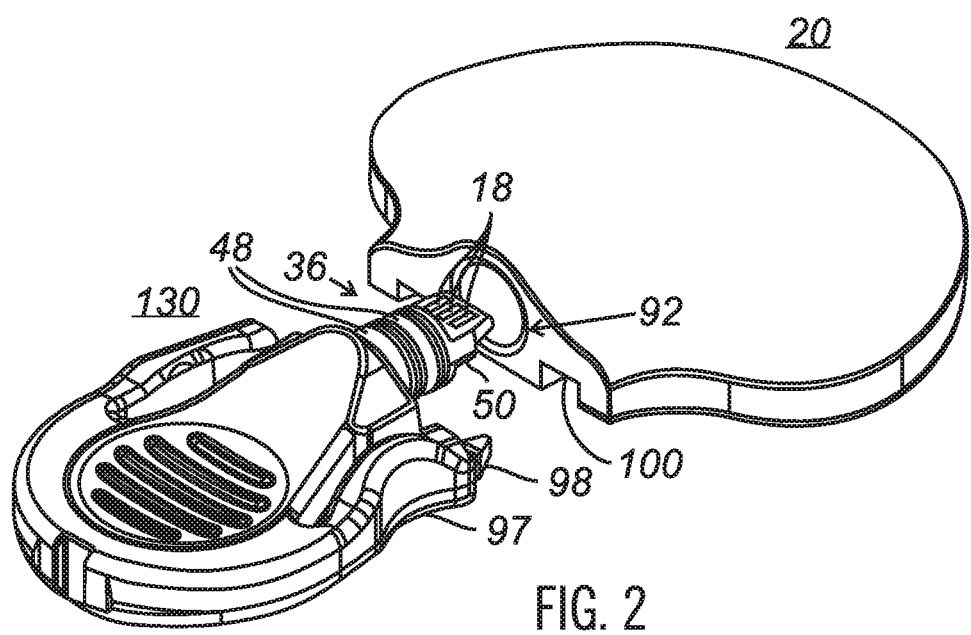
FIG. 2 illustrates a perspective view of a connector and test plug.

The connector 20 may also be used with a test plug 130, one embodiment of which is shown, in FIG. 2. Such a test plug 130 may have the same general configuration as regards its connector fitting 36 with respect to the connector 20 connections as does the mounting base 30 shown in FIG. 1. The arrangement of FIG. 2 however shows an important alternative arrangement for the connector fitting 36. Such connector fitting 36 can also be used as for the mounting base of FIG. 1. In the FIG. 2 arrangement as well as the removal of the lower half of the key 50 forming a flat surface parallel to the axis of the tubular element 42, a flat surface is formed by removing a sector from the shape of the upper surface of the key 50. The key 50 thereby has a rounded side trapezium shape in cross-section. This arrangement is also shown in FIGS. 19-23 and described below in more detail. The pair of flat surfaces facing in opposite directions enable the test plug of FIG. 2, or the mounting base of FIG. 1, when provided with the FIG. 2 connector fitting 36 to be supported from both sides within the connector 20. Also, this arrangement allows for connection to a foil with a greater number of contacts as the connector foil can wrap around the end of the key. This provides one set of contacts on the lower surface and another set of contacts on the upper surface. In that case, a stabilizing and centralizing force can be provided via the contacts within the connector 20. When attached to the sensor connector 20, the test plug shown in FIG. 2 provides a tight seal by virtue of the "O" seal rings 48, allowing a patient to wash those components without the danger of water entering the socket 92. This is particularly useful in the embodiments with wireless transmitters, especially those that are sealed within the connector 20. Like the mounting base 30, the test plug 130 includes a key 50, adapted to slide into the socket fitting 92 of the connector 20. The test plug 130 also includes latch arms 97 and latch tips 98, which can interact with latch recesses 100 on the connector 20. When the test plug 130 is coupled to the connector 20, the latch tips 98 lock into the latch recesses 100. They can be released by pressing on the latch arms 97 so that the connector 20 can be removed. In practice, a sensor kit as sold commercially may comprise a connector, a mounting base and a test plug, where the connector is configured to be connectable physically and electrically compatible with both the test plug and the mounting base.

For the sake of uniformity, there is herein continual reference to the "tubular element" 42 forming part of the connector filling 36 in both the case of the mounting base and the test plug. It is however envisaged that the tubular element be solid (i.e. with no bore through it). This may be the case if all of the circuitry for the test plug is mounted on the contact foil, or in the case of the sensor if connection to the distal end need not pass right through the element.

The test plug 130 also allows for testing of wireless transmitters or other sensor electronics in the connector 20 without receiving data from any sensor. Thus sensor electronics can be tested alone and without external sensor noise. For example, the test plug may be a simple tester that generates a single current, such as 53.5+/−10%) that can be detected by sensor electronics and read by a monitoring device. In certain embodiments, the tester shorts the reference and counter electrodes, which are discussed herein.

Figure 3:
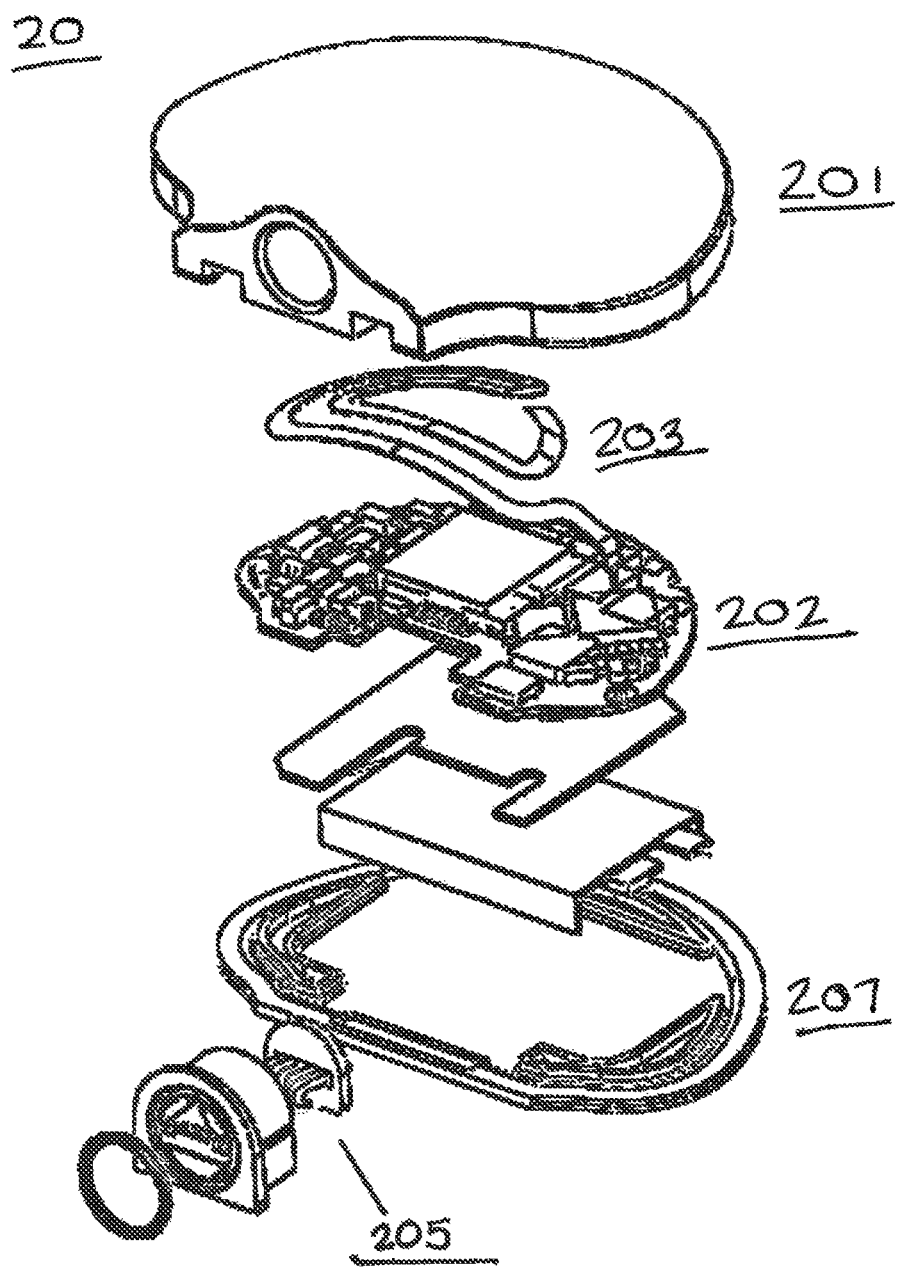
FIG. 3 illustrates an expanded view of a connector with wireless sensor electronics.
Figure 4:
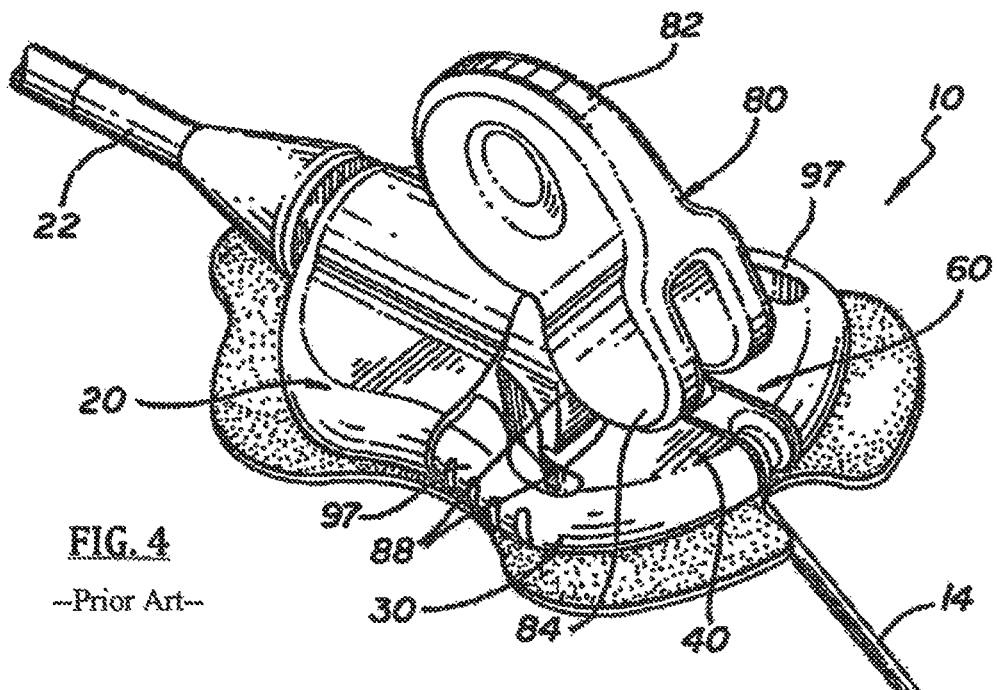
FIG. 4 illustrates a perspective view of a sensor set with insertion tool.
Figure 5:
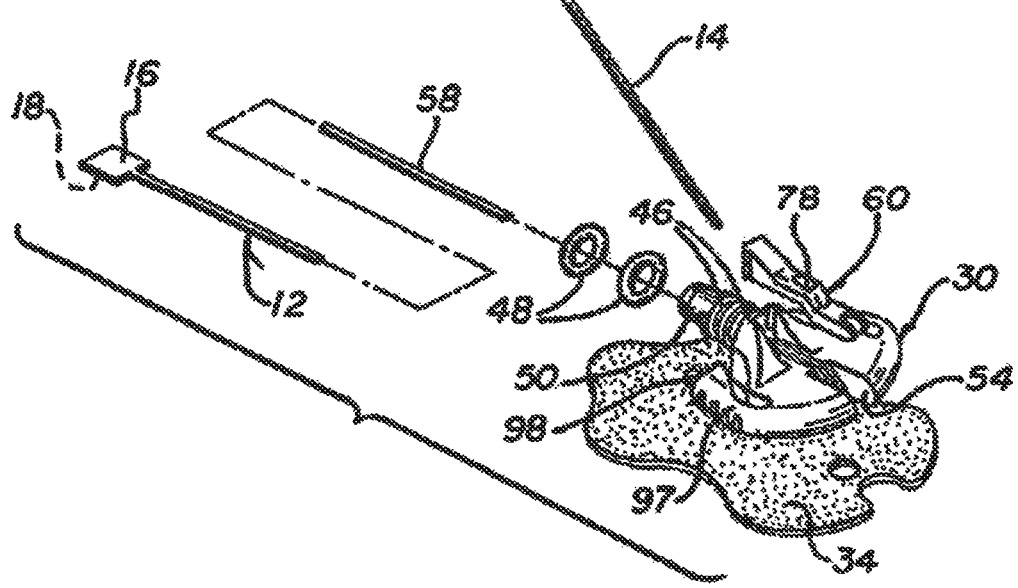
FIG. 5 illustrates an expanded view of a mounting base, including sensor, and insertion tool.

An example connector 20 is shown in FIG. 3, which includes sensor electronics with a wireless transmitter. A housing consists of an upper shell housing portion 201 and a lower shell housing portion 207. The housing encases a circuit board 202 and an antenna 203. The circuit board can include an application specific integrated circuit (ASIC). Although one preferred antenna shape is shown in FIG. 3, but other configurations are contemplated that could allow for fitting a suitable antenna in the connector. A contact plug/pin housing 206 holds molded pins 205 and sits inside the housing 201/207 forming the interior of the socket 92 such that when the sensor mounting base 30 is connected to the connector 20, the sensor electronics on the circuit board 202 can receive signals from the sensor housed in the mounting base 30 and the mounting base 30 is held securely and stably in contact with the connector 20 by virtue of the profile of the key 50 on the connector fitting 36. Sensor electronics including wireless transmitters are discussed, for example, in U.S. Pat. No. 7,602,310, which is herein incorporated by reference.

As an alternative in the arrangements described with respect to FIGS. 1 and 2 the connector may comprise a termination of a cable wired directly to a monitor, which may or may not include a display. It may include only a wire connector or may include some sensor electronics that also include a wire connector, depending on the needs of the user.

The connector 20 may include a rechargeable power source, such as a rechargeable battery. The rechargeable power source may be charged using a charger that holds the connector or is otherwise coupled to the connector to recharge the power source. Example chargers are shown, for example, in U.S. patent application Ser. No. 12/434,076, filed on May 1, 2009, which is herein incorporated by reference.

The sensor set and any related monitor may be of the type suitable for determining glucose levels in the body and/or body fluids of the user and may be used in conjunction with automated or semi-automated medication infusion pumps of the external or implantable types as described in U.S. Pat. Nos. 4,562,751, 4,678,408, 4,685,903, and 4,573,994, which are herein incorporated by reference, to deliver insulin to a diabetic patient. However, it will be recognized that the invention may be used in arrangements to determine the levels of other agents, characteristics or compositions, such as hormones, cholesterol, medication concentrations, pH, oxygen saturation, viral loads (e.g., HIV), or the like. The sensor set may also include the capability to be programmed or calibrated using data received by the sensor electronics, or may be calibrated at the monitor device. The sensor system is primarily adapted for use in subcutaneous human tissue. However, it may be placed in other types of tissue, such as muscle, lymph, organ tissue, veins, arteries or the like, and be used in animal tissue. It will be understood that the term "patient" can be broadly construed to encompass humans and other animals, and that the term "blood" encompasses patient blood and other extracellular patient fluids. Embodiments may provide sensor readings on an intermittent or continuous basis.

The sensor set primarily discussed herein uses an electrode-type sensor. However, the system may use other types of sensors, such as chemical based, optical based or the like. The sensors may be of a type that is used on the external surface of the skin or placed below the skin layer or the user. Certain surface mounted sensors could utilize interstitial fluid harvested from underneath the skin.

Where the connector has sensor electronics including a wireless transmitter, the sensor electronics generally include the capability to transmit data. Alternatively, these sensor electronics may include a receiver or the transmitter may be a transceiver with the capability to receive data. FIGS. 4-18 show a direct connection to a wire that can carry signals to separate sensor electronics, which may include a monitor or display and may also (or alternatively) transmit data to an external monitor or display.

As shown in FIGS. 6-8, the flexible thin sensor 12 foil comprises a relatively thin and elongated element which can be constructed according to so-called thin mask techniques to include elongated conductive elements 24 (FIG. 6) embedded or encased between layers of a selected insulative sheet material such as polyimide film or sheet. In some embodiments, the flexible thin sensor may be contained in a flexible tube to provide support. However, it is possible for a thicker sensor to be stiff enough to facilitate sensor to base assembly and to reduce instances of sensor kinks without a flexible tube. A thickness of about 17-40 μm is sufficiently thick to provide this stability, for example 25 μm. The proximal end or head 16 of the sensor 12 is relatively enlarged and defines the conductive contact pads 18, which are exposed through the insulative sheet material for electrical connection to the cable 22, as will be described in more detail. An opposite or distal segment of the sensor 12 includes the corresponding plurality of exposed sensor electrodes 15 for contacting patient body fluid when the sensor distal segment is placed into the body of the patient. The sensor electrodes 15 generate electrical signals representative of patient condition, generate electrical signals representative of patient condition, wherein these signals are transmitted via the contact pads 18 and connector, which may include sensor electronics (wired or wireless) or just a connection to a wire, to an appropriate monitoring device (not shown) for recordation and/or display to monitor patient condition. Further description of flexible thin film sensors of this general type may be found in U.S. Pat. No. 5,391,250, which is herein incorporated by reference. Further description of wired sensor electronics may be found in U.S. Pat. No. 7,602,310, which is herein incorporated by reference.

In addition to the methods shown in the patents incorporated herein by reference, it is possible to fabricate the sensor with a no-pre-plating wet etching process or a pulsed+DC plating process, which allows for uniform platinum morphology. In an enzyme entrapment method, the glucose oxidase (GOx) enzyme is entrapped within a photosensitive polymer that crosslinks upon UV exposure. With this type of photosensitive polymer, the need for a glutaraldehyde crosslink step is eliminated, providing the ability to have the enzyme only over the sensing working electrodes through selective curing of the photosensitive polymer.

The sensor 12 is carried by the sensor set, specifically on the mounting base 30, which is adapted for placement onto the skin of a patient (FIGS. 17-18) at the selected insertion site. The sensor set generally comprises a compact mounting base 30 having a generally planar or flat underside surface 32 (FIGS. 7-8) attached to an adhesive patch 34 for press-on adhesive mounting onto the patient's skin. The patch may be sized such that it has as much adhesion to skin as possible while not being too large for comfort or to easily fit on a patient. The adhesive patch may be made from a material with stretch to increase comfort and to reduce failures due to sheer. It is understood that alternative methods for attaching the mounting base to the skin of a patient, other than an adhesive patch, also may be contemplated. The mounting base 30 is generally constructed out of lightweight plastic so that it may be comfortably worn throughout numerous activities by a patient. The mounting base 30 may be constructed as a unitary molding of lightweight plastic to include a connector fitting 36 for slide-fit coupling with the sensor connector 20, which may include a wireless transmitter, wired electronics, or merely a cable for connection to external sensor electronics and/or monitor. A bore 44 through the connector fitting 36 leads to an upwardly open recessed groove or channel 38 formed in an upper surface 40 of the mounting base 30 (e.g., FIG. 6) to receive and support the sensor 12 between its proximal end or head 16 and its distal end.

FIGS. 5-8 show a mounting base 30 to comprise a rearwardly projecting tubular element 42 defining a central bore 44 aligned generally coaxially with a rearward end of the recessed channel 38. The tubular element 42 includes external grooves 46 (FIG. 5) for receiving seal rings 48 adapted for sealed slide-fit engagement with the cable connector 20, as will be described. The rearward end of the tubular element 42 terminates in a key 50 formed as a rearward extension thereof comprising a "D" section with a pair of flat surfaces of the apex of its curved back. The key thus has flat surfaces extending parallel to the axis of the tubular element on each side and facing away from each other. When engaged with the connector the flat surface comprising the straight side of the "D" supports contact pads 18 against spring contacts within the connector, while the pair flat surfaces corresponding to the material removed from apex of the "D" engage with a structure within the connector providing stability and a reaction force.

Figure 28:
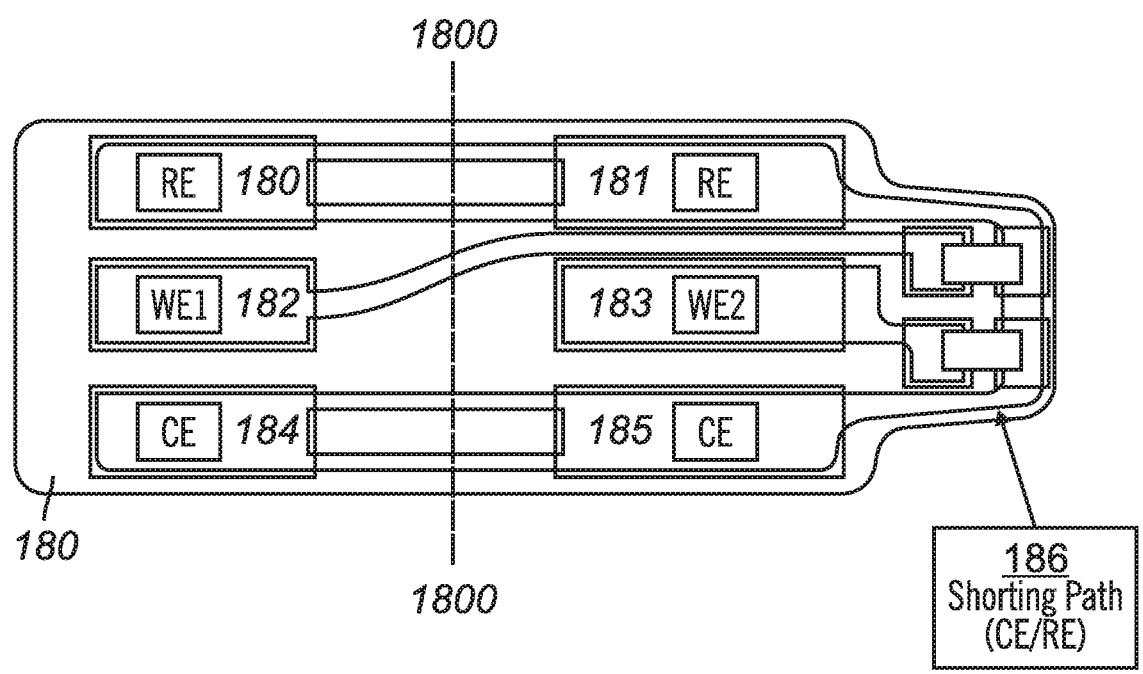
FIG. 28 illustrates a diagram of contact pads for a sensor.
Figure 29:
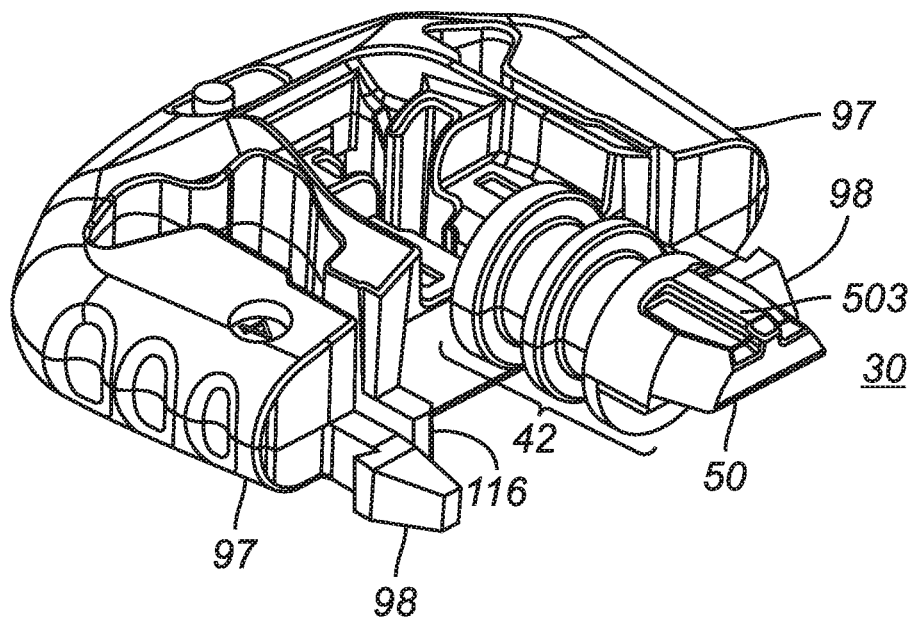
FIG. 29 illustrates a perspective view of a mounting base.

FIGS. 19-23 show coupling arrangements in respect of a test plug and connector. Identical arrangements are envisaged, however for corresponding mounting bases. In the description that follows both the mounting base and the test plug variants will be discussed. In the case of the mounting base the contacts referred to contacts on the proximal end of a sensor leading to electrodes directly or via circuitry mounted in the electrodes. In the case of the test plug the electrodes are the electrodes of test circuitry. The configuration or layout of the contacts is identical for the test plug and the actual sensor as is apparent from the description below referring to FIG. 28.

Figure 19:
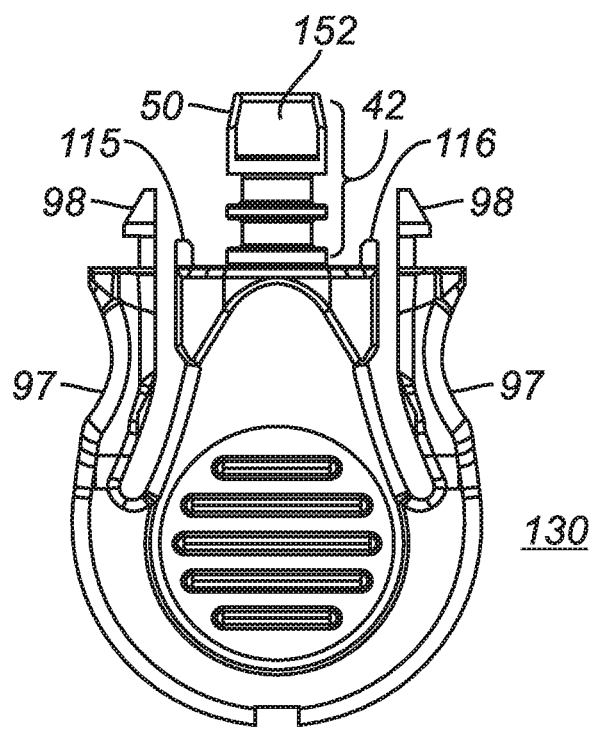
FIG. 19 illustrates a top view of a test plug.
Figure 20:
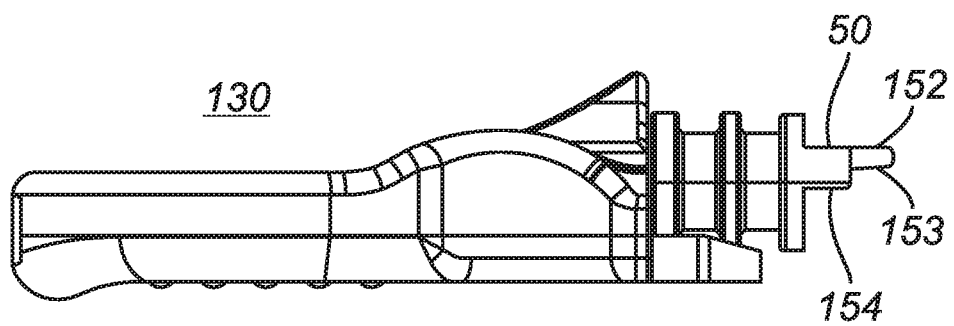
FIG. 20 illustrates a side view of a test plug.
Figure 21:
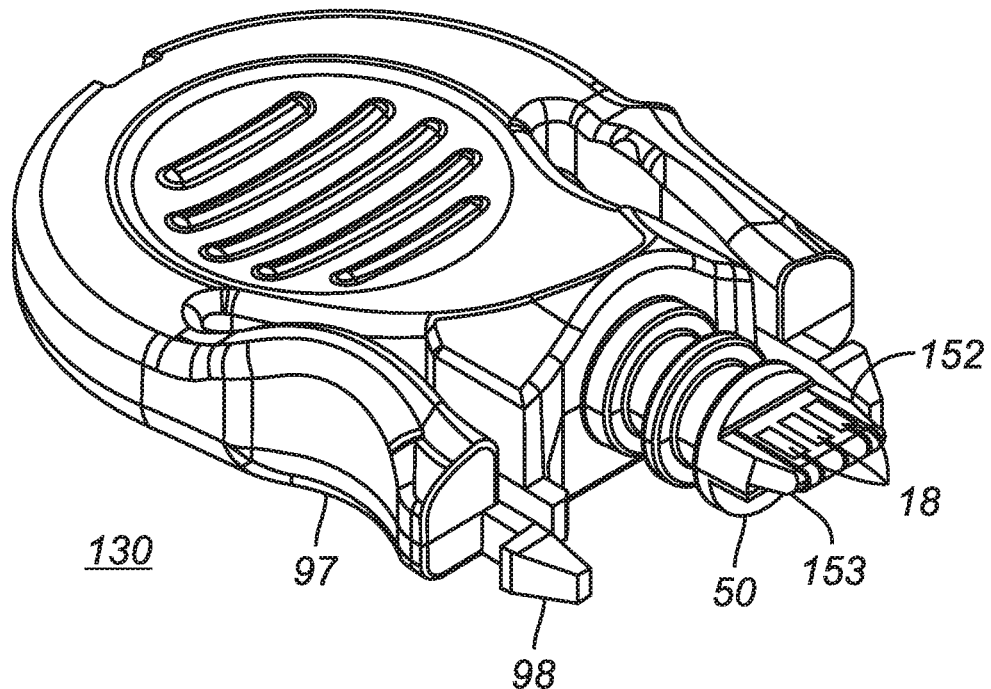
FIG. 21 illustrates a perspective view of a test plug.

As shown in FIGS. 19-21, the top and the bottom of the key 50 are each substantially flat and each incorporate shallow flats or seats 152 and 153. The recessed seats are sized and shaped to receive and support a flexible test circuit, or in the case of the mounting base as shown in FIG. 9, the proximal head 16 of the sensor 12, with the proximal end of the elongated sensor 12 extending from said head 16 through the bore 44 and lying within the recessed channel 38. The recessed seats may include a shelf 154 (FIG. 20) that allows the bottom of the key to step from a narrow depth to a slightly wider depth. This shelf allows for the unique fitting of current keys into only compatible connecting pieces on sensor connectors, which include matching recesses. The shelf further improves tolerance and robustness of the connections. As can be seen in FIG. 21, the proximal head 16 of the flexible test circuit or of the sensor 16 may be configured such that it folds around the key 50 so that the contacts are on both seats 152 and 153. In this configuration, the flexible test circuit or the proximal head 16 of the flexible test circuit or of the sensor may include 2 sets of contact pads 18. For example, in FIG. 28 one embodiment of a schematic for the contact pads is shown. The contact pads shown are two for a reference electrode (180, 181), two for a counter electrode (184, 185), and one for each of two working electrodes (182, 183).

A shorting path 186 allows for a shorted reference electrode/counter electrodes and a resistor may be used to account for additional working electrode(s) and counter electrode(s). By allowing for additional contact pads in the same space, additional electrodes may be used in the sensor without requiring additional size of the mounting base or connector. In the configuration showed in FIG. 28, the fold of the substrate 180 is generally along the line 1800-1800 so that one set of contact pads is on each side of the key 50. In alternative embodiments a single set of contacts could be included on just one side of the key 50, as shown in other embodiments herein.

Figure 23:
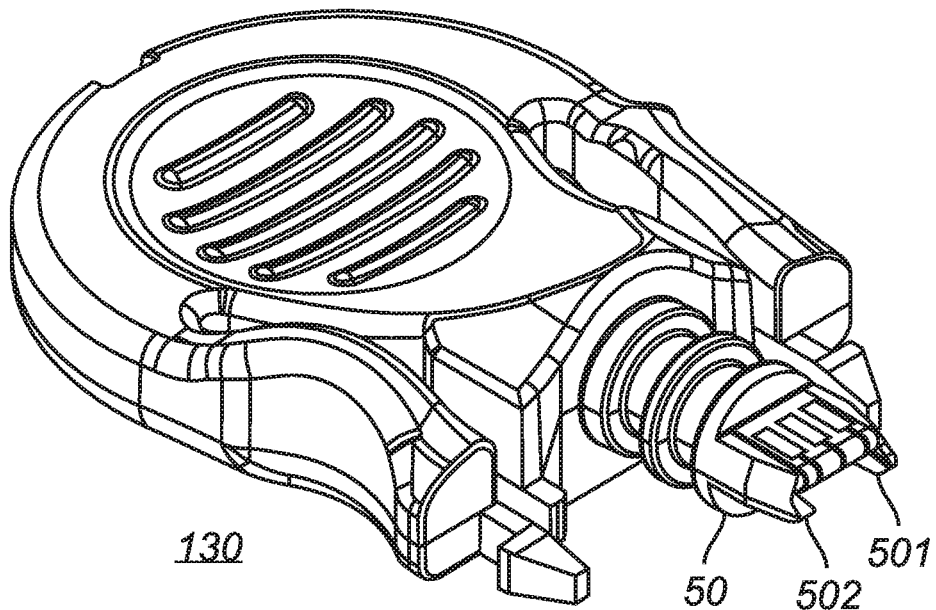
FIG. 23 illustrates a perspective view of a test plug.
Figure 31:
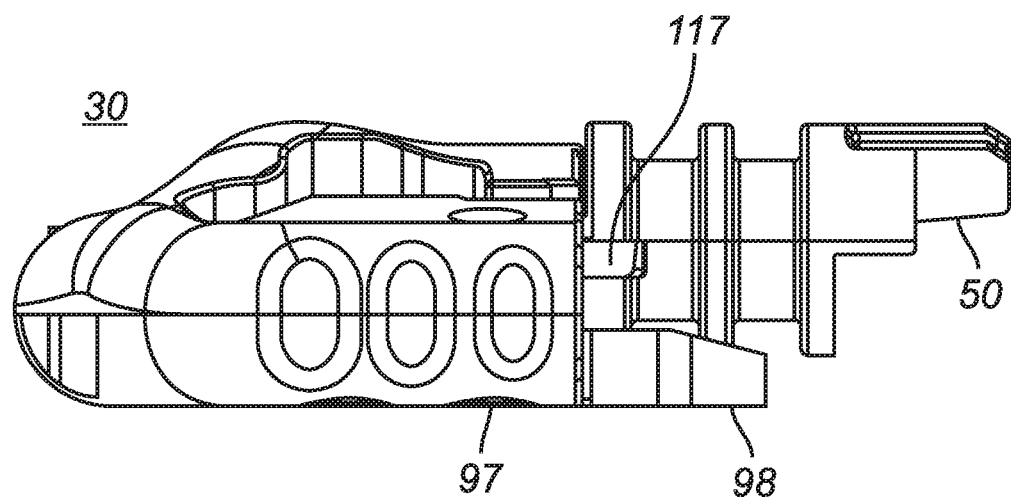
FIG. 31 illustrates a side view of a mounting base.

As shown in FIG. 23, the key 50 may include prongs 501 and 502 that fit into respective prong recesses in the connector (not shown) and lockout other non-compatible connectors. The prongs also help assist in rotational stability of the coupling and assist in ensuring a good connection between the connector and mounting base. Respective prong recesses in the connector are shown in FIG. 31 (a partial view of the connector).

In alternate embodiments, shown for example in FIG. 8, the rearward end of the tubular element 42 terminates in a generally D-shaped or half-circle fitting key 50 with a pair of cut-outs at its top formed as a rearward extension of the tubular element and which incorporates a shallow recessed flat or seat 52 formed at the rearward end of the bore 44. The recessed seat 52 receives and supports the proximal head 16 of the sensor 12.

Figure 24:
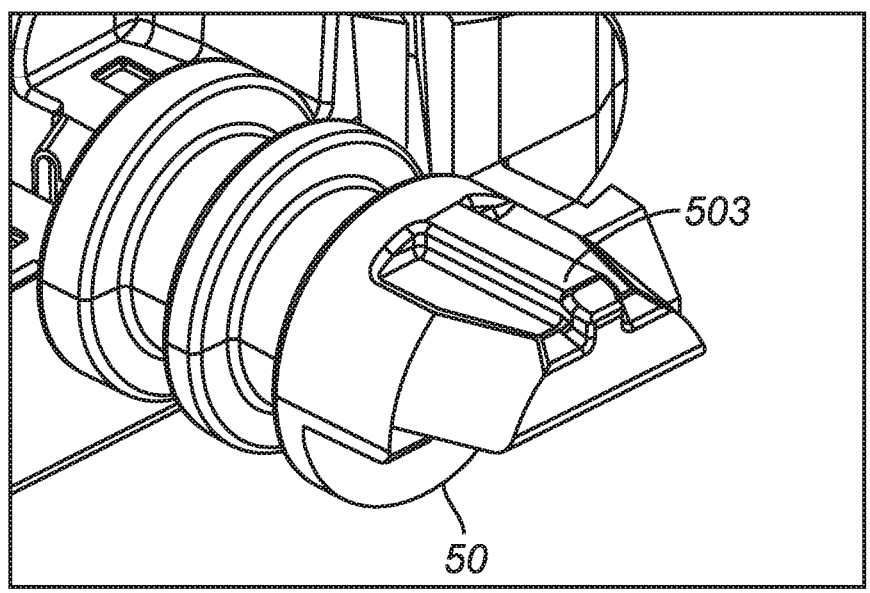
FIG. 24 illustrates a partial perspective view of a mounting base or test plug.

In still further embodiments, the rearward end of the tubular element 42 terminates in a generally D-shaped or half-circle fitting key 50 that has been cut out on top to form a rail 503 (as shown in FIG. 24). This rail 503 corresponds to a trench 125 (as shown in FIG. 25B) in the mounting base. The rail provides additional stability and prevents other non-compatible components, which do not include the rail/trench configuration, from coupling with components that have the rail/trench configuration.

In embodiments, the head 16 of the sensor 12 is secured and seated within the recessed seat(s) 52 or 152, 153 by means of a suitable adhesive or the like. In addition, subsequent to placement of the sensor 12 through the bore 44, the bore 44 may be hermetically sealed with suitable sealant such as curable silicone sealer or the like.

For facilitated slide-fit engagement with the sensor connector 20, the seat 52 may be formed to ramp angularly rearwardly and upwardly from a central axis of the bore 44, thereby supporting the sensor head 16 with the contact pads 18 presented downwardly and angularly rearwardly.

Because it is possible for both configurations of keys discussed above to exist in various mounting bases of differing compatibilities, the key further serves to prevent use of one configuration of mounting base 30 with the other configuration of connector 20. Thus, the key allows to ensure compatibility of sensors to connectors and to related monitors and prevents chemically or technically incompatible parts from being used with each other.

Figure 10:
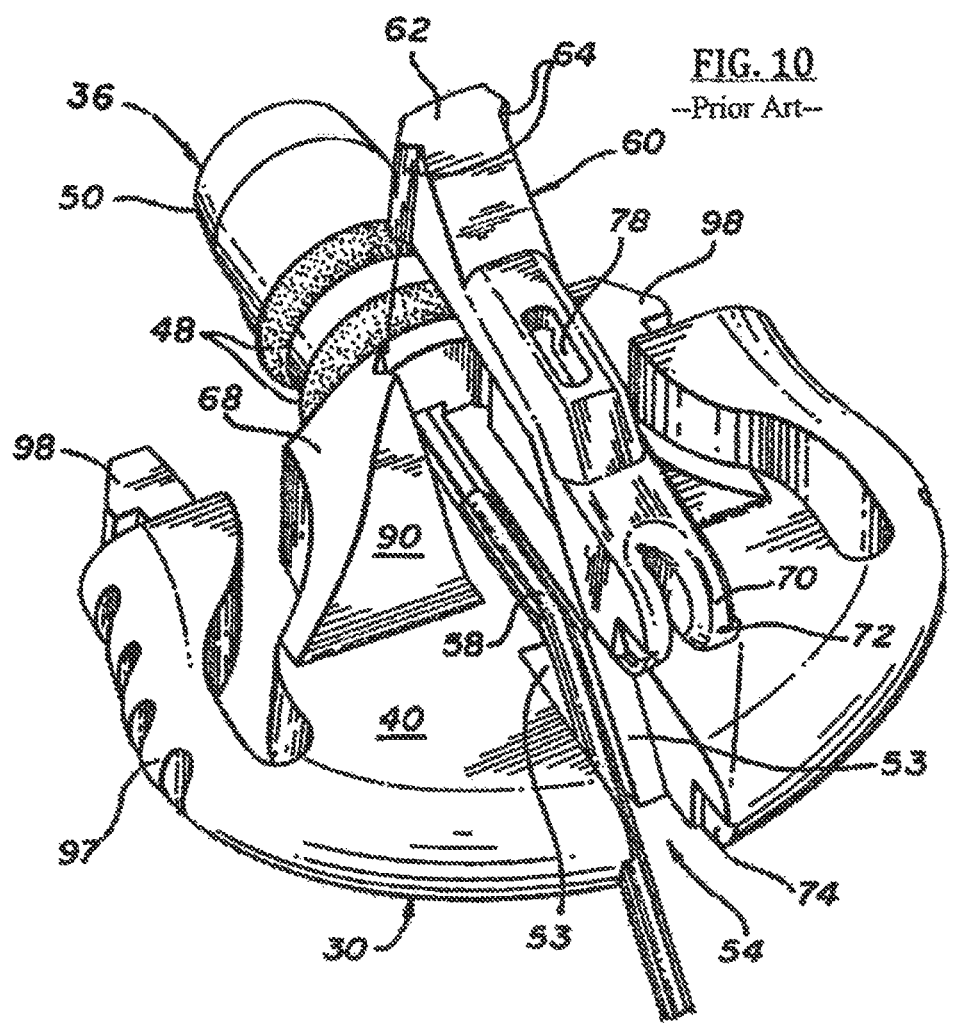
FIG. 10 illustrates another expanded view of a mounting base with retainer cap.
Figure 11:
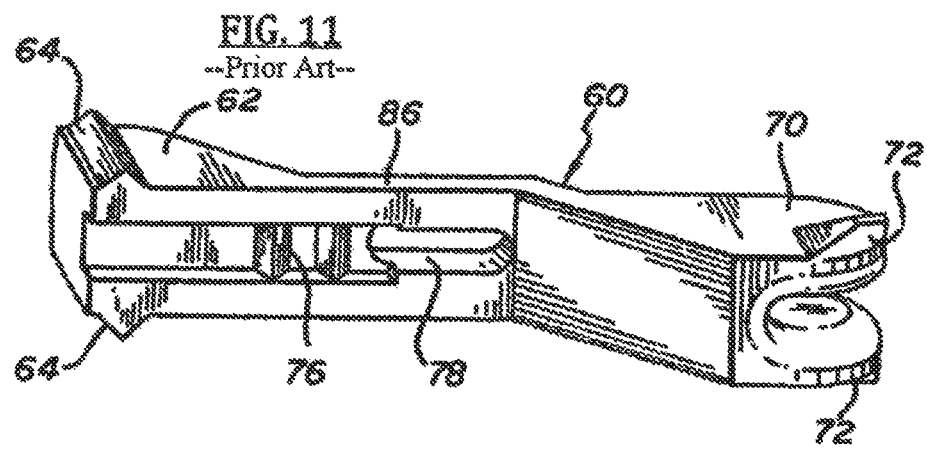
FIG. 11 illustrates an underside view of the retainer cap of FIG. 11.
Figure 12:
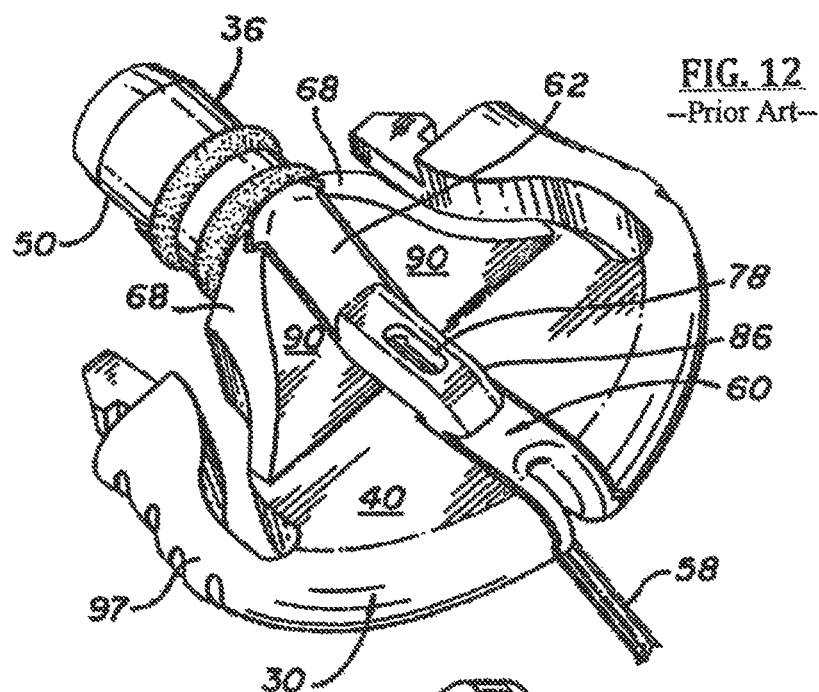
FIG. 12 illustrates a perspective view of a mounting base with retainer cap.
Figure 13:
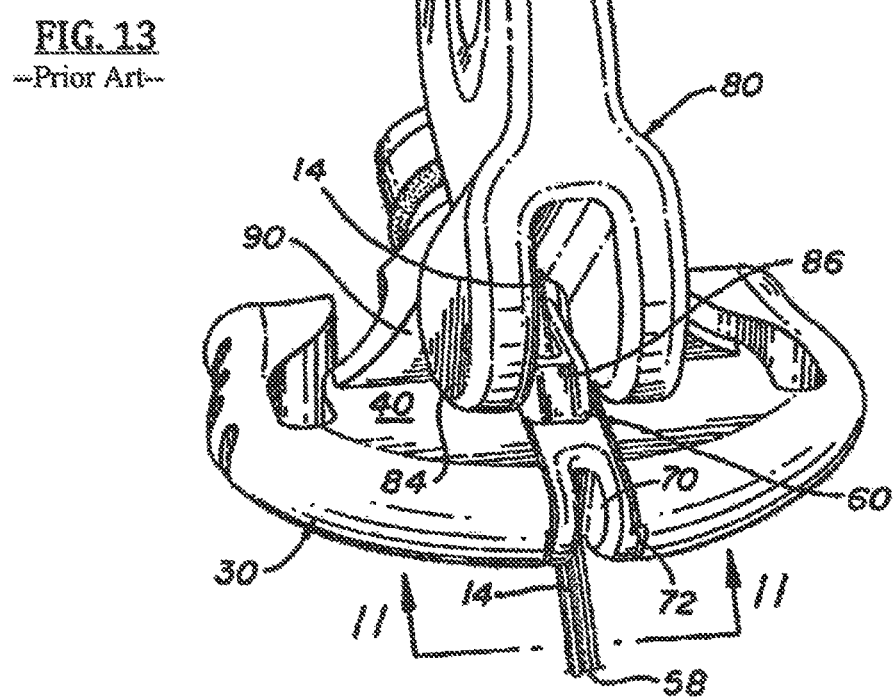
FIG. 13 illustrates a perspective view of an insertion needle installed on an assembled mounting base and retainer cap.
Figure 17:
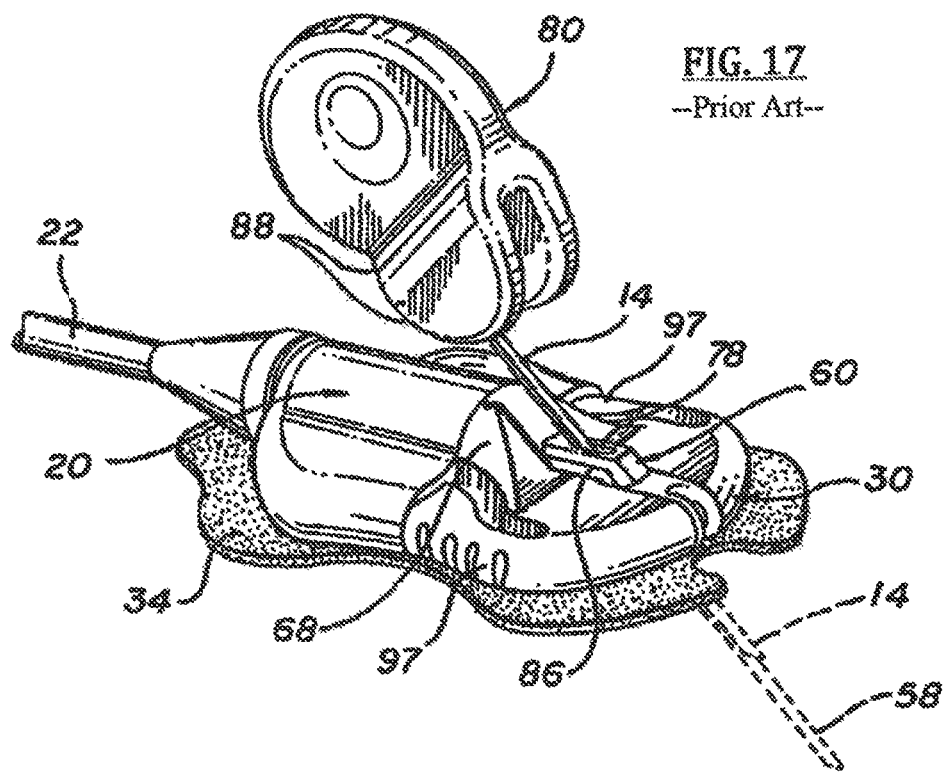
FIG. 17 illustrates a perspective view showing sliding removal of the insertion needle from a sensor set, following placement of the mounting base onto the skin of a patient.
Figure 18:
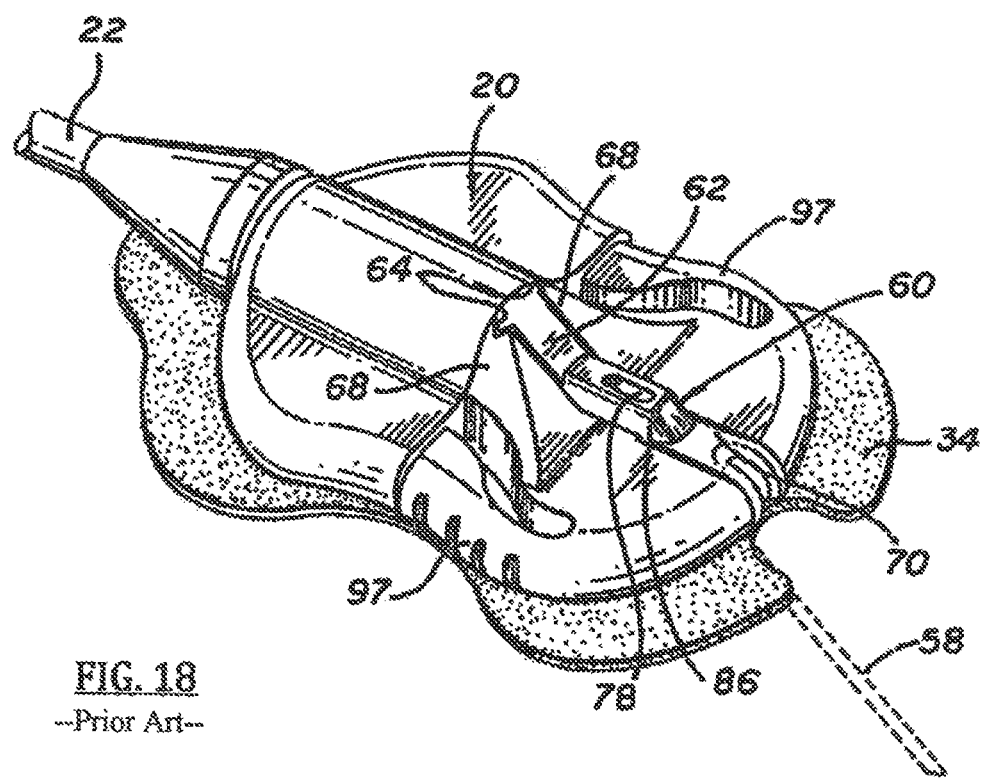
FIG. 18 illustrates a perspective view showing a sensor set and cable connector mounted onto the skin of a patient, following removal of the insertion needle.

In embodiments, the recessed channel 38 in the mounting base 30 thus receives and supports the proximal segment of the thin film sensor 12. As shown in FIGS. 6, 9 and 10, the recessed channel 38 extends forwardly from the fitting bore 44 with a generally horizontal orientation, and then turns downwardly and forwardly at an angle of about 45 degrees to extend along an angled face 53 within a forwardly open gap 54 formed in the front end or nose of the mounting base. In some embodiments, a cannula 58 is slidably fitted over at least a portion of the proximal segment of the sensor 12, to extend also over the distal segment to encase and protect the sensor. In the preferred form, the cannula is constructed from a lightweight plastic material such as a urethane based plastic, and has a double lumen configuration. The double lumen cannula 58 is especially suited for slide-fit engagement with and disengagement from the insertion needle 14, as will be described in more detail, and includes a window 59 to expose the sensor electrodes 15. The specific cannula construction for receiving and supporting the sensor 12, and for slidably interfitting with the insertion needle 14, is shown and described in more detail in U.S. Pat. No. 5,586,553, which is herein incorporated by reference.

In further embodiments, an insertion method is included as part of the sensor set. For example, a retainer cap 60 allows for insertion of the sensor set. In embodiments, the proximal end of the sensor 12 and the portion of the cannula 58 thereon are folded as shown in FIG. 10 to follow the contour of the mounting base channel 38, so that the distal segment of the sensor and the cannula thereon extend and protrude downwardly and forwardly from the front of the mounting base 30. The sensor and cannula may be captured and retained in this orientation by a retainer cap 60 shown in FIGS. 10-12. This retainer cap 60 also may be formed conveniently and economically as a lightweight plastic molding and includes means for quick and easy snap fit installation onto the mounting base 30. When the retainer cap 60 is assembled with the mounting base 30, these components cooperatively close the top of the channel 38 to capture and retain the sensor and cannula therein. The retainer cap 60 further defines a needle port 78 (FIGS. 12 and 13) for pass through reception of the insertion needle 14. The insertion needle 14 has a hollow and longitudinally slotted configuration (FIG. 14) with a pointed or sharpened tip and a rear end anchored to an enlarged hub 80. The hub 80 is manually manipulated to fit the needle 14 through the cap port 78, in order to slide the slotted needle into engagement with the cannula 58 within the forwardly and downwardly angled portion of the channel 38. In this regard, the needle port 78 is sized and shaped to orient the insertion needle 14 for proper angular and rotational alignment with the cannula 58 to ensure correct slide-fit engagement therebetween.

More particularly, the hub 80 includes an enlarged tab-like wing 82 adapted for easy grasping and handling between the thumb and index finger. This enlarged wing 82 projects upwardly from a bifurcated nose 84 which is sized and shaped to seat onto the mounting base upper surface 40, on opposite sides of a raised central section 86 of the retainer cap 60. The hub nose 84 is contoured to defined keyed alignment or guide surfaces 88 for matingly contacting associated keyed alignment surfaces on the mounting base 30, defined by the upper surface 40 and an angularly presented forward face 90 of the support brackets 68. With this geometry, the hub 80 is slidably displaced against the mounting base 30 with the insertion needle 14 extending into and through the cap port 78 at the correct angular and rotational orientation for slide-fit engagement with and disengagement from the cannula 58. In the preferred form, the insertion needle 14 slidably assembles with the cannula 58 as described in U.S. Pat. No. 5,586,553, which is herein incorporated by reference, to provide a generally circular cross sectional profile (FIG. 14) protruding from the mounting base.

FIGS. 15-16 show the connector 20 for coupling with the assembled insertion set 10. A cable connector is used for wired connection to a monitor or display. The connecting components of the cable connector can instead be on a connector including sensor electronics that allow wired or wireless transmission to a monitor or display. As shown, the cable connector 20 comprises a compact coupling element which can also be constructed from lightweight molded plastic. The cable connector 20 defines a socket fitting 92 for mating slide-fit engagement with the rear cable fitting 36 of the mounting base 30. This socket fitting 92 has a cylindrical entry portion 93 which merges with a generally D-shaped or half-circle step portion 94 sized to receive the D-shaped key 50 of the fitting 36. Flat bottomed inserts provided at the top of the cylindrical socket provide reaction against the flats at the top of the "D" section in FIGS. 6-13. As shown, the socket fitting 92 includes a plurality of conductive contacts 96 (FIG. 15) positioned on the step portion 94 for electrically coupled engagement with the contact pads 18 on the sensor 12 in the case of the mounting base embodiments or the contact pads 18 on the test circuit in the case of the test plug embodiments, when the insertion set 30 or test plug 130 and cable connector 20 are coupled together. Referring to FIG. 16, when assembled, seal rings 48 sealingly engage the entry portion 93 of the socket fitting 92 to provide a sealed connection between the components. The geometry of the interfitting components 50 and 94 ensure one-way interconnection for correct conductive coupling of the cable 22 to the sensor 12.

Figure 37:
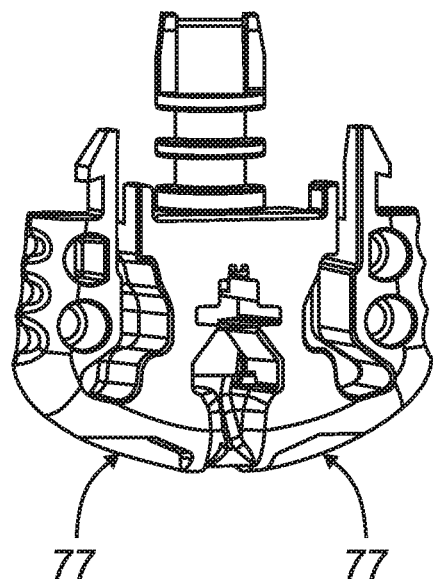
FIG. 37 illustrates a perspective view of a test plug.

More advanced insertion tools may also be used to insert the sensor into a patient. Insertion tools that can interact with the mounting base of the present invention are shown, for example, in U.S. Pat. Nos. 5,851,197, 6,093,172, and 6,293,925, which are herein incorporated by reference. In embodiments, as shown in FIG. 37, the mounting base includes one or more inserter cutouts 77 to interact with an insertion tool, making the interaction more specific to certain insertion tools. The inserter cutouts 77 may also allow for better stability during insertion.

Figure 38:
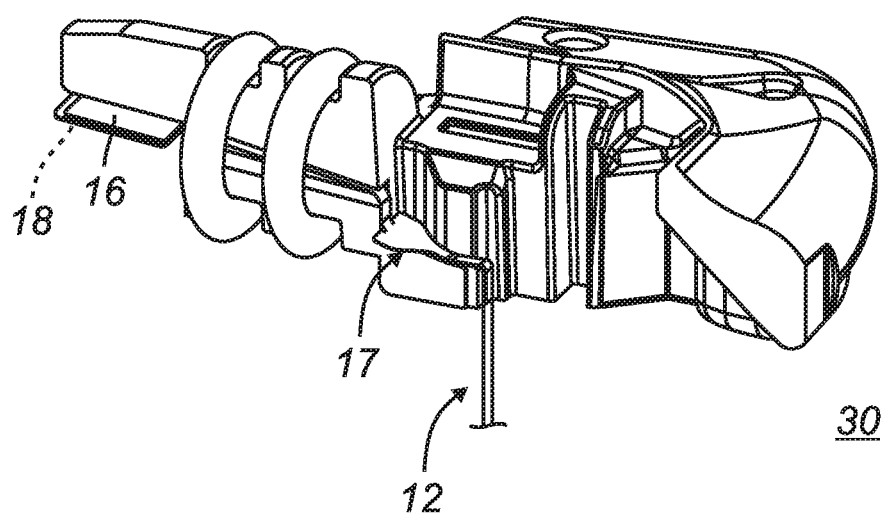
FIG. 38 illustrates an internal, partially cut-away view of a mounting base with sensor.

In further embodiments, a shim may be installed in the mounting base 30, as shown in FIG. 38 (a partial cut-away view). The shim 17 in installed as part of the sensor 12 to prevent pull-up. It minimizes friction between the sensor and the needle during insertion, eliminates room for motion within the cavity of the mounting base, and improves sensor rigidity along the vulnerable neck-down region of the mounting base.

Figure 25A:
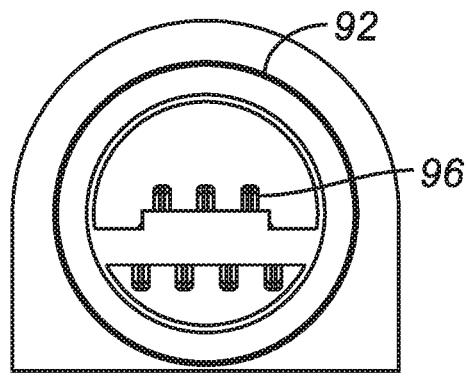
FIGS. 25A-C illustrate sectional views taken along a socket fitting of a mounting base.
Figure 25B:
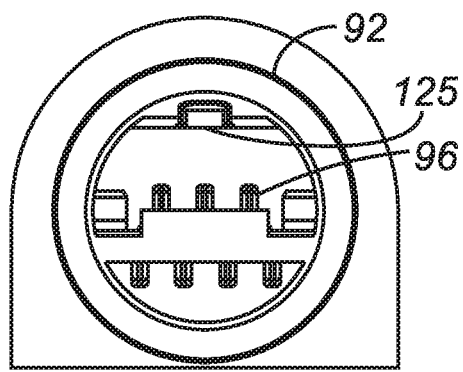
Figure 25C:
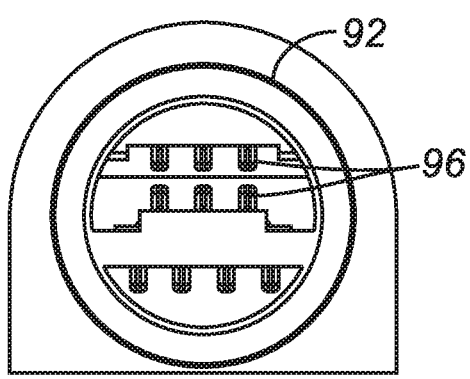
Figure 25D:
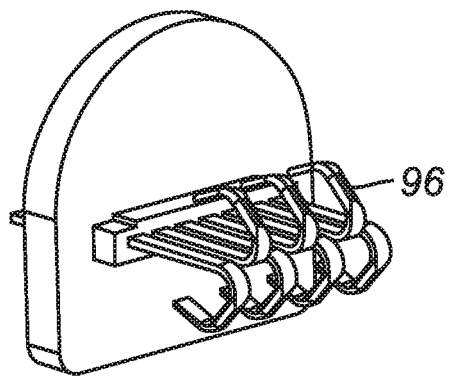
FIGS. 25D-E illustrate perspective, expanded views of pins used as contacts in a mounting base.
Figure 25E:
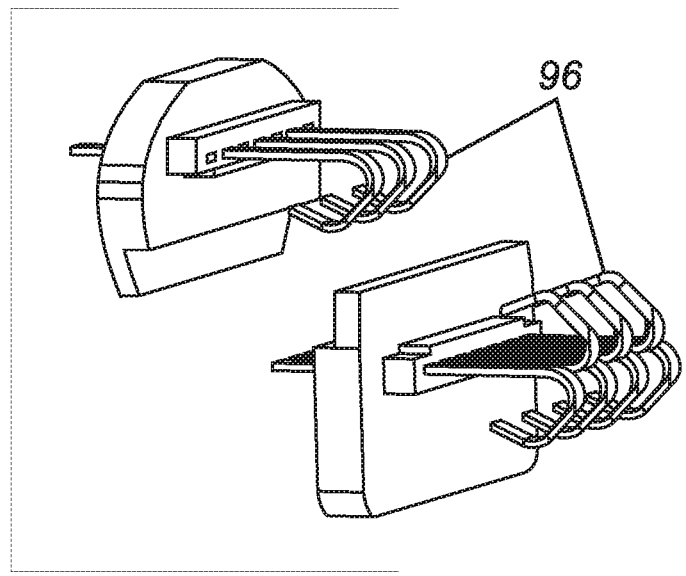
Figure 25F:
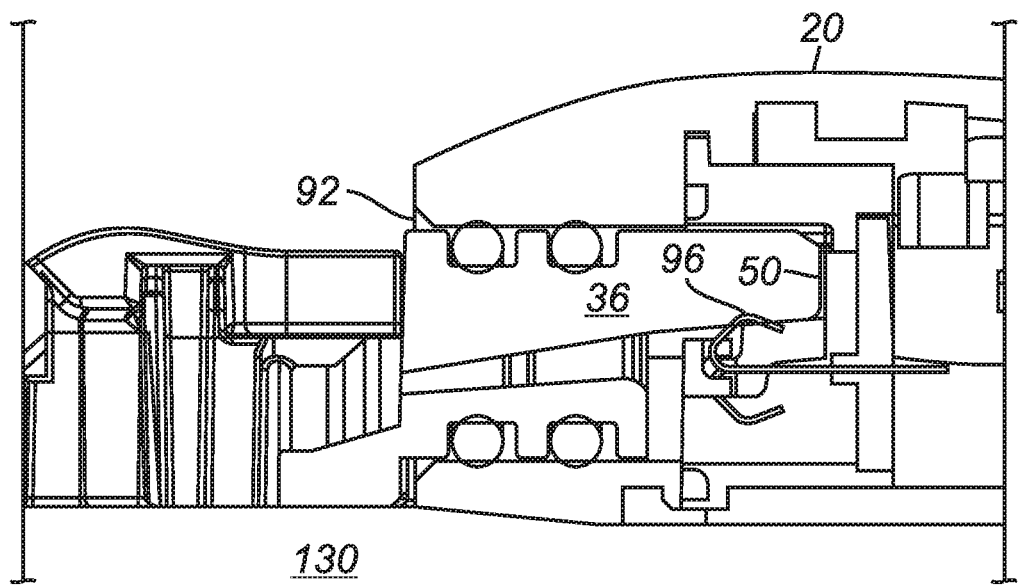
FIG. 25F illustrates a cut away view of a test plug.

Several embodiments of the conductive contacts 96 are shown in FIG. 25A-F. While certain numbers of conductive contacts are shown in these figures, and corresponding numbers of sensor contact pads are shown in other figures herein, it is contemplated that different numbers of conductive contacts and corresponding sensor contact pads could be used as long as they are sufficient to determine data related to the sensed body characteristic. FIG. 25A-C show cut-away views of the socket fitting 92 with the interior conductive contacts 96. FIG. 25A shows the fitting of a generally D-shaped portion 94 with two flats at the top (FIGS. 4-18) and with the conductive contacts 96 being pins that touch the contact pads of the key 50 when the key is fit into the socket fitting 92. FIG. 25B shows another embodiment where the D-shape has been slightly cut away and a railing added that fits into the runner 125. The runner 125 allows for both blocking the non-compatible components from being used with this sensor connector but also gives additional stability, such as rotational stability. FIG. 25C shows an embodiment where the conductive contacts are on both sides of the key, so that there are 2 sets of pins 96 that will contact the conductive contacts. Further views of the conductive pins are shown in FIG. 25D (pins from FIGS. 25A and 25B) and in FIG. 25E (pins from FIG. 25C, shown in expanded form). FIG. 25F shows an embodiment of a test plug 130 fitting into a connector 20. The form of the pins allows for some compression of the pins when the key is inserted into the socket. Unlike in a situation with 2 non-flexible contacts that need exact molding so that they touch each other, this compression gives assurance that the contact pads will contact the pins every time. In addition, the pins will provide additional stability while they push into the contact pads of the key 50.

The mounting base 30 and the cable connector 20 are retained in releasably coupled relation by interengaging snap fit latch members. As shown in FIGS. 15 and 16, for example, the mounting base 30 is formed to include a pair of rearwardly projecting cantilevered latch arms 97 which terminate at the rearward ends thereof in respective undercut latch tips 98. The latch arms 97 are sufficiently and naturally resilient for movement relative to the remainder of the mounting base 30, to permit the latch arms to be squeezed inwardly toward each other. The permissible range of motion accommodates snap fit engagement of the latch tips 98 into a corresponding pair of latch recesses 100 formed in the cable connector 20 on opposite sides of the socket fitting 92, wherein the latch recesses 100 are lined with latch keepers 102 for engaging said latch tips 98. The components can be disengaged for uncoupling when desired by manually squeezing the latch arms 97 inwardly toward each other for release from the latch keepers 102, while axially separating the mounting base 30 from the cable connector 20.

Figure 34:
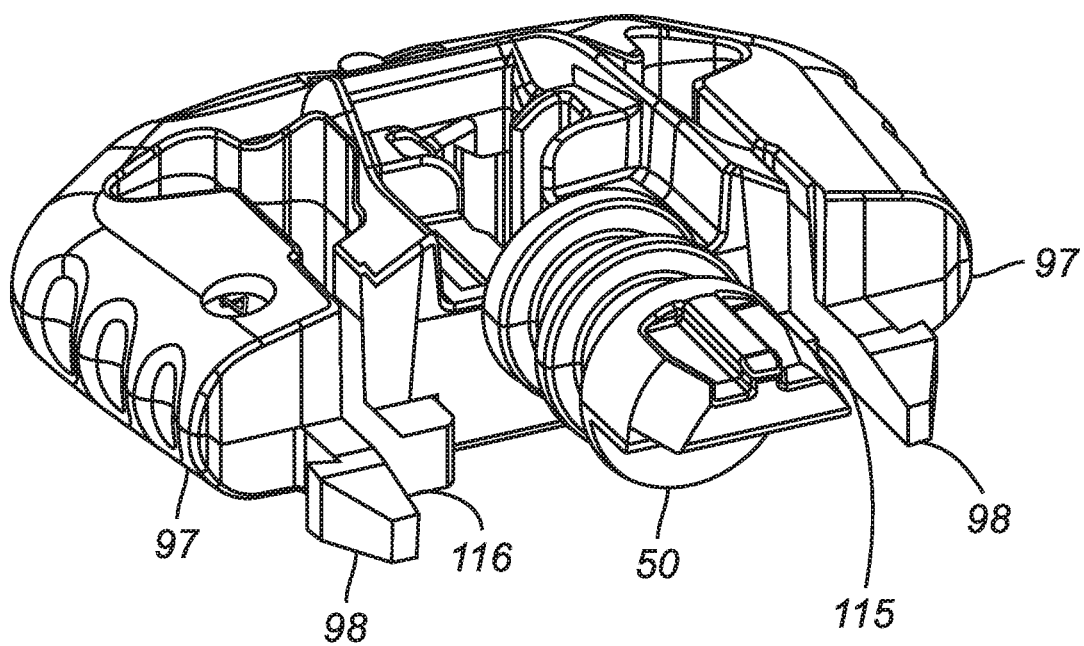
FIG. 34 illustrates a perspective view of a mounting base.

Further as shown in FIGS. 19 and 34 the test plug 130 (not shown in FIG. 34) or mounting base 30 (not shown in FIG. 19) includes anti-rotation arms 115 and 116. In certain embodiments, as in FIG. 19, the anti-rotation arms are generally adjacent to the tubular element 42, which includes the key 50. The connector 20 (partially shown in FIG. 22) includes anti-rotation arm recesses 215 and 216, which correspond and fit with the anti-rotation arms. In the embodiment shown in FIG. 22, the connector also includes catch recesses 217 and 218, which can catch anti-rotation arms if they are formed with hooks, like the latch tips 98 of the test plug/mounting base. These anti-rotation components help to prevent rotation of the mounting base 30 and test plug 130 with respect to the connector 20 and also help to ensure that the connector is only used with compatible test plugs and mounting bases, avoiding compatibility issues of physical or technical nature. In further embodiments, the width and/or height of the anti-rotation arms may be varied to lock-out previous non-compatible components. An anti-rotation arm on each side of the tubular element prevents rotation may provide additional stability. Each anti-rotation arm prevents rotation around the other anti-rotation arm as well as around the tubular element. Such anti-rotation arms may be incorporated on any of the test plugs or mounting bases described herein. Alternatively, in any such arrangements the anti-rotation arms 115, 116 can be provided on the connector 20 and the corresponding recesses 215, 216 can be provided on the test plug 130 or mounting base 30.

From the arrangement described with reference to FIGS. 19-22 it can be seen that the invention also provides, according to a further aspect, a connection arrangement to couple a mounting base of a subcutaneous sensor or a test plug substitute for the mounting base, to a connector. Such connection is typically needed to communicate the electrical signals from the sensor to external equipment, for example, a display for blood glucose level or an infusion pump in the case where the system is being used for diabetes management. The connection arrangement comprises a body of the mounting base or test plug, said body having a mating surface on one side. The connector has a connector interface forming part of the connection arrangement with a complementary mating surface to that of the said body. Protruding from the mating surface of the body is a probe 42 with contacts on the end thereof. The connector interface has a socket sized to receive the probe 42 and containing contacts to connect with the contacts on the end of the probe when the connection arrangement is engaged. On each side of the probe also protruding from the mating surface are a pair of anti-rotation posts 115, 116 each spaced from the probe 42. On the complementary surface of the connector interface there is a recess 215, 216 on each side of the probe into which the anti-rotation posts 115, 116 fit. Typically, the recess is much wider than the post, extending further beyond the socket such that the anti-rotation post, if it engages the wall of the recess at all, engages the wall closest to the probe and socket. The body also has a pair of resilient latch arms 97, 98 which emerge from the body at points remote from the mating surface and continue parallel to the body towards the mating surface. These latch arms then extend beyond the mating surface in the form of upstanding latch posts 98 with outwardly facing chamfered tips. The latch arms 97, 98 are resilient they have a relaxed position in which the latch tips 98 are splayed, and a compressed position where the latch tips are moved together, thus reducing the distance between the resilient arms and the body. The recesses 215, 216 in the complementary surface, one on each side of the probe are wide enough to accommodate, in addition to the anti-rotation posts 115, 116 the latch posts. Each recess has an outer wall on its side away from the probe, the outer wall having undercuts complementary to the latch tips of the latch arms such that with the arms in the relaxed position and hence the tips in the splayed position the latch tips fit in said undercuts and is prevented from withdrawal by the narrower mouth portion of the slot obstructing the latch posts. Hence separation of the mating surface and the complementary mating surface is prevented. Squeezing the two latch arms together however moves them to the compressed position where the latch tips can escape from the undercuts of the recess and the mating surfaces can be separated. Thus, on each side of the probe 42 on the body there are two pairs of posts, one inward pair being responsible to prevent rotation. These rise from the mating surface immediately adjacent the probe and hence due to the stiffness of the body easily resist any tendency for the probe to rotate. A second pair of posts separated by an air gap from the anti-rotation posts are for latching. Their triangular tips latch into recesses in the outer walls of the recesses in the complementary surface which form an undercut. These latching posts are on the end of resilient arms connected further back on the body of the mounting base or test plug. Typically they are made of the same material as the mounting base or test plug body, but because they are relatively thin they are resilient. Squeezing the arms together reduces the air gap between the latch posts and the anti-rotation posts, making the combination narrow enough to escape the narrower mouth due to the undercut and exit the mouth of the recess in the complementary surface. Thus, the latch arms provide resilience and the anti-rotation posts provide stability against rotation and both engage the same pair of recesses in the complementary surface, thus reducing production costs and resulting in the generally simpler design.

Figure 26:
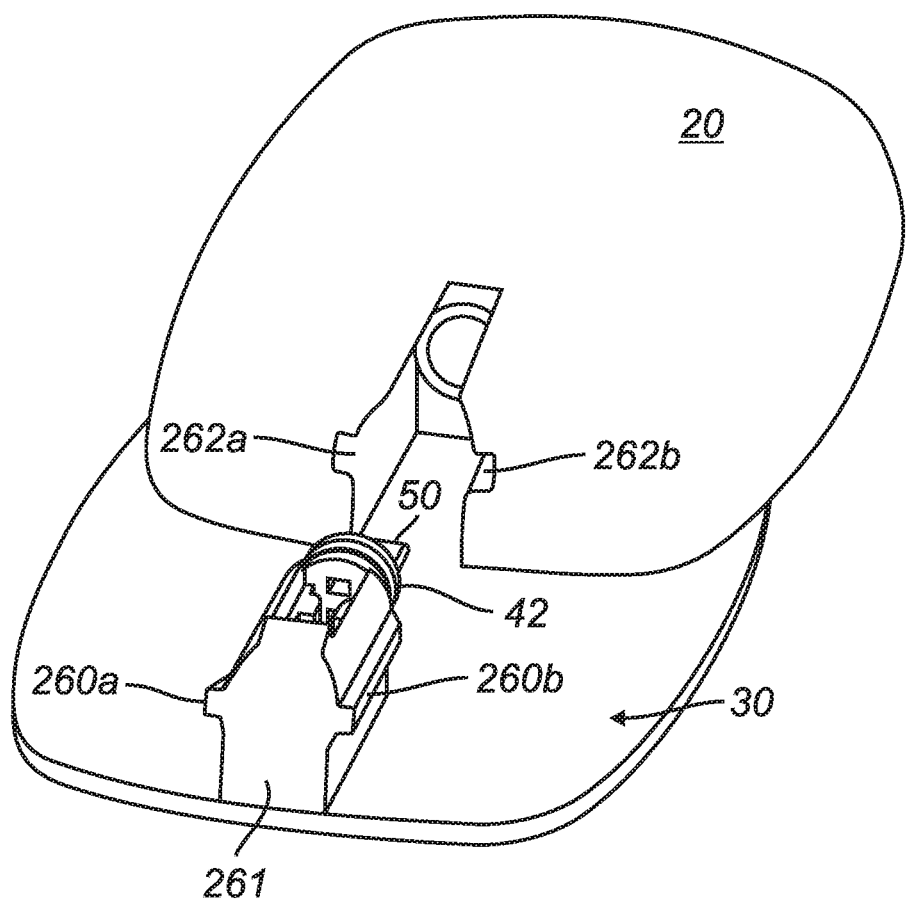
FIG. 26 illustrates a perspective view of a mock-up showing the connection between a connector and a test plug or a mounting base.

FIG. 26 shows a system connecting a mounting base 30, with a layer of adhesive on its underside and typically supporting a subcutaneous sensor, to a connector 20, which may comprise a transmitter sending data from the sensor via a wireless link to monitoring equipment. The coupling of the connector 20 with mounting base 30 may comprise a connector fitting 36 of the mounting base 30 extending into the connector 20. The mounting base 30 has an upstanding post 261, from which extends a tubular element 42. The tubular element 42 and a fitting key 50 of the connector fitting 36 may fit into the connector 20 to connect it to the mounting base 30. Once connected, the profile of the transition from the mounting base 30 to the connector 20 is smooth.

It is desirable to provide stability of the system when coupled, as well as prevent connection with (known as locking out) incompatible components. This is achieved in the FIG. 26 arrangement using side rails and slots. The housing of the connector 20 may have horizontal side rails which engage with horizontal slots on the mounting base 30. More preferably, an upstanding post 261 of the mounting base 30 may have horizontal side rails which engage with horizontal slots in the housing of the connector 20. Slots each have an entrance at one end and a transverse end block at the other end. Side rails each have a length less than that of the distance from the entrance to the end block of their respective slot. This allows engagement of the correct side rail with its corresponding slot, but not of a side rail and slot in which the side rail is longer than the distance from the entrance to the end block of the slot.

FIG. 26 shows side rails 260*a* and 260*b* on the mounting base 30 that engage with slots 262*a* and 262*b* in the connector 20. Side rail 260*a* and its corresponding slot 262*a* may be the same length or different lengths to side rail 260*b* and its corresponding slot 262*b*. FIGS. 27A-27F show various examples of combinations of side rail lengths that could be used to lock out different versions of the mounting base 30 and connector 20. FIGS. 27A and 27F, for example, show side rails 272 and 273 with a great difference in length. FIGS. 27B and 27E show side rails 272 and 273 with a less great difference in length, whilst FIGS. 27C and 27D show side rails 272 and 273 with little difference in length. The side rails may also be of the same length as each other. The length of side rail 272 is set up to match the distance between the entrance and end block 270, whilst the length of slide rail 273 is set up to match the distance between the entrance and end block 271 of its corresponding slot, so that a mounting base 30 with either rail length longer than the distance of its corresponding slot will not engage with connector 20.

Thus, the FIG. 26 arrangement illustrates a system connecting a mounting base 30, typically supporting a subcutaneous sensor, to a connector 20 which typically contains a transmitter sending data from the sensor via a wireless link, wherein the mounting base 30 comprises a platform having on one side an adhesive layer for attachment to a patient, and on the other side a post 261 with a tubular element 42 extending therefrom parallel to the platform, the connector 20 having a housing with a socket positioned to engage the tubular element 42 by means of sliding rails and slots which engage with one another, characterized in that the slots each have an entrance at one end and a transverse end block at the other end and the side rails each have a length less than that of the distance from the entrance to the end block of their respective slot, allowing for lock out of incompatible mounting bases and connectors where at least one side rail is longer than the distance from the entrance to the end block of its corresponding slot. The system of FIG. 26 may incorporate the coupling arrangements previously described to provide further stability, as discussed above.

Figure 22:
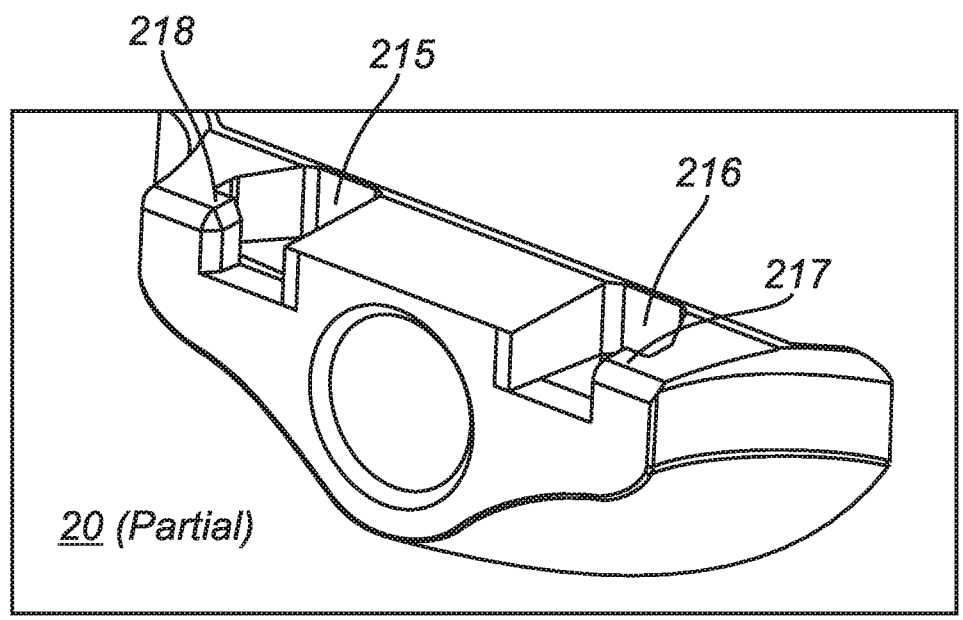
FIG. 22 illustrates a partial perspective view of a connector.
Figure 35:
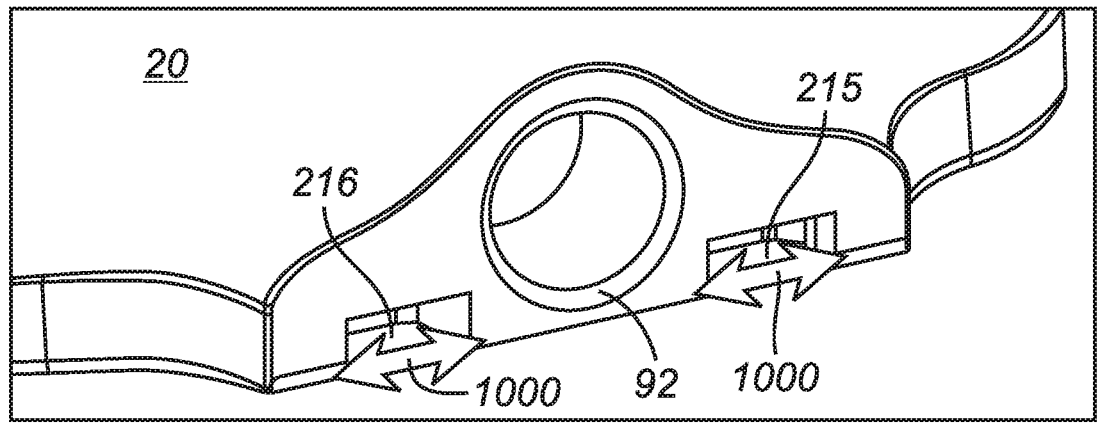
FIG. 35 illustrates a partial perspective view of a connector.

In the embodiment shown in FIG. 22, the connector also includes catches 217 and 218, which can catch anti-rotation arms if they are formed with hooks, like the latch tips 98 of the test plug/connector. These anti-rotation components help to prevent rotation of the mounting base/test plug and connector with respect to each other and also help to ensure that the mounting base is only used with compatible test plugs/mounting bases, avoiding compatibility issues of physical or technical nature. In further embodiments, the width and/or height of the anti-rotation arms may be varied to lock-out previous noncompatible components. As shown in FIG. 34, it may be preferable for the anti-rotation arms 115, 116 of the mounting base 30 or test plug (not shown) to be at least as wide as they are tall to increase stability and further ward against rotation. If the anti-rotation arms are at least as wide as they are tall, they cannot be easily crushed or defeated and are less likely to fold over when pressure is applied. FIG. 35 shows a partial view of a connector 20 with widened rotation-arm recesses 215 and 216, which also act as latch recesses for the latches on the mounting base/test plug. The arrows 1000 are not part of the connector 20 and are merely demonstrating that the rotation arm recesses 215 and 216 have been widened to allow for the wider anti-rotation arms shown in FIG. 34.

With respect to the anti-rotation arm recesses, it is possible to have the anti-rotation arm recesses be separate and distinct from the latch recesses 100. However, in the figures shown herein, both the latches and the anti-rotation arms fit into the rotation arm recesses 215, 216, such that the latch tips of the mounting base/test plug engage with the catches 217 and 218 (shown in FIG. 22), and so that the latch recesses 100 and latch keepers 102 for engaging the latch tips 98 are the same feature as the rotation arm recesses 215, 216 and catches 217, 218.

Figure 30:
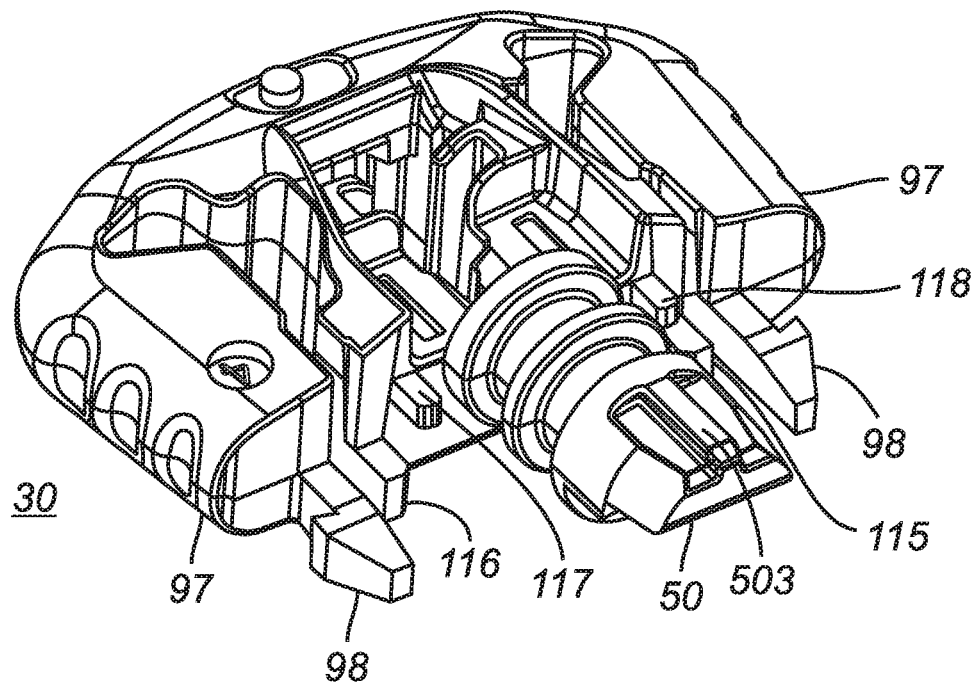
FIG. 30 illustrates a perspective view of a mounting base.
Figure 32:
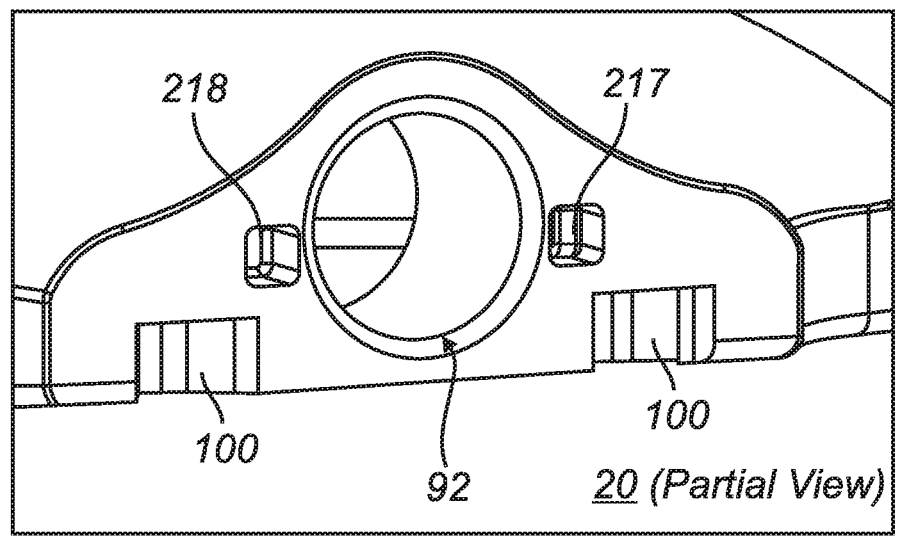
FIG. 32 illustrates a partial perspective view of a connector.
Figure 33:
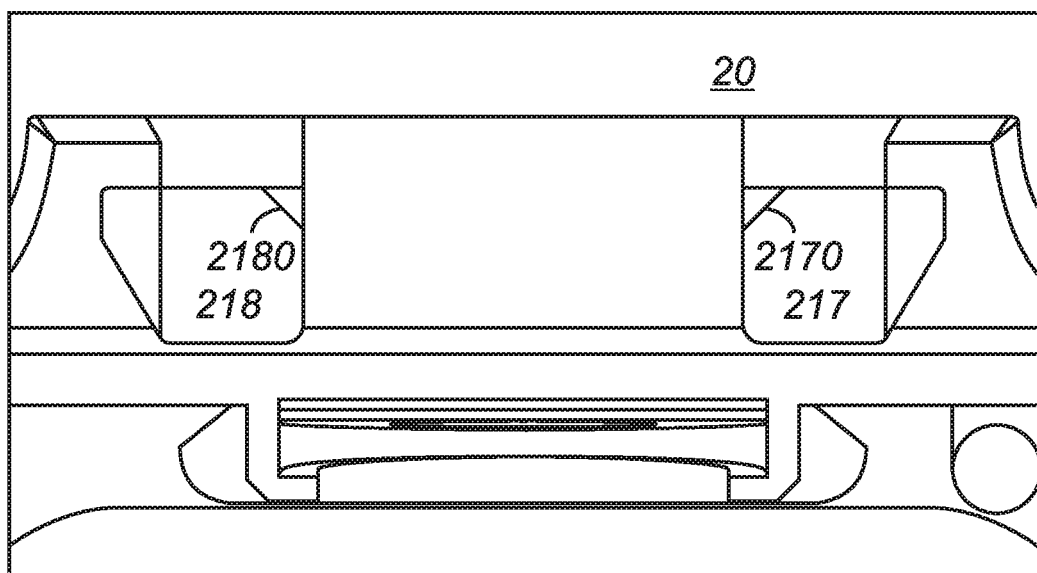
FIG. 33 illustrates a partial, close-up side view of a connector.

In further embodiments, additional elements are included to provide stability and lockout from incompatible components. For example, FIGS. 30 and 31 show a mounting base 30 with lockout pillars 117 and 118. These lockout pillars 117 and 118 interact with and slide into lockout pockets 217 and 218 in the connector 20, as shown in FIGS. 32 and 33 (both showing partial views of the connector 20). The test plug (not shown) may be similarly modified to include lockout pillars that can slide into the lockout pockets 217 and 218. When the mounting base/test plug is connected to the connector, the lockout pillars further prevent rotation between the components. In addition, they prevent the mounting base/test plug being used with incompatible connectors that do not have the matching lockout pockets (and, vice versa, they prevent use of connectors with incompatible mounting bases/test plugs). Although 2 lockout pillars are shown in FIG. 30, it is possible to have any reasonable number of lockout pillars that correspond with an equal number of lockout pockets on the connector.

The lockout pockets may be shaped by boring out a portion of the connector, through injection molding of all or part of the connector, or through other methods of molding or formation of plastic parts known in the art. The lockout pillars and lockout pockets are preferably constructed such that the lockout pillars fully fit into the lockout pockets when the test plug or mounting base is connected to the connector, when latch tips 98 fully engaged in the latch recesses 100, thus ensuring a tight connection of the test plug/mounting base with the connector. This tight connection improves water resistance, stability of parts and proper connection of electronic components. In further embodiments, material may be added into the pockets to create a more unique shape. This more unique shape may be used to increase stability or to create a better lockout system using more specific interlocking components with more particular shapes. Material can be added or removed to facilitate cleaning by changing the shape of pocket. Other benefits of changing the shape of the pocket is to help inform the user which lockout configuration they have or to allow sets of lockout configurations. One of these configurations is shown in FIG. 33, where the added material 2170, 2180 is shown in the lockout pockets. The added material may be made from the same material as the rest of the connector or a different material suitable for adding to the lockout pockets 217, 218. Polycarbonate and polycarbonate blends (PC/ABS, PC/PBT, e.g.) are well suited for added material because of their mechanical toughness and ability to survive common sterilization methods, such as e-beam and ETO. However, any thermoplastic that is no-compressible would be sufficient as a material.

Additional embodiments are contemplated to provide stability and/or lockout from incompatible components. For example, in FIG. 26, a mock-up of the connecting portions of a mounting base and connector are shown, where the mounting base includes side rails 260 that fit into slots 262 in the connector. FIGS. 27A-27F show various examples of combinations of side rail lengths that could be used to lock out different versions of the mounting base and connector. As can be seen, the lengths of the rails are set up to match the lengths of the slots so that a mounting base with the incorrect rail lengths will not fit into a connector. In this configuration, the sensor set forms a base plate on which the connectors rest, thus giving the connector and base plate the same footprint, producing a more compact design. The connector slides onto the sensor unit, which is upstanding on the base plate with the coupling within the body of the connector, thus providing more stability in the connected condition, and it is less likely for the items to become accidentally separated in use. The entire structure has a smooth profile helping to reduce accidents, and the sliding engagement has rails of varying and different lengths (as per FIGS. 27A-27F), meaning that a connector must be suited to the particular sensor unit for it to engage properly.

In additional embodiments, the position of the anti-rotation arm extensions may be varied with respect to the main body/central section of the test plug/mounting base. As an example, FIG. 19 shows a top view of a test plug 130 with a main body/central section 35. The tubular element 42 extends from the main body of the test plug. Extending from this main structure/central section are the anti-rotation arms 115 and 116. The latch arms 97 are attached to yet separate from the central section of the mounting base or test plug, so that they may be compressed toward the central section 35 when latching into the latch recesses 100 on the connector 20. When the mounting base or test plug connects to the connector, the latch arms 97 move toward the central section until the latch tips 98 are fully within the latch recesses 100 (or recesses 217, 218), snapping into place and locking the mounting base/test plug from disconnecting away from the connector until a user wishes to disconnect the components.

Figure 36:
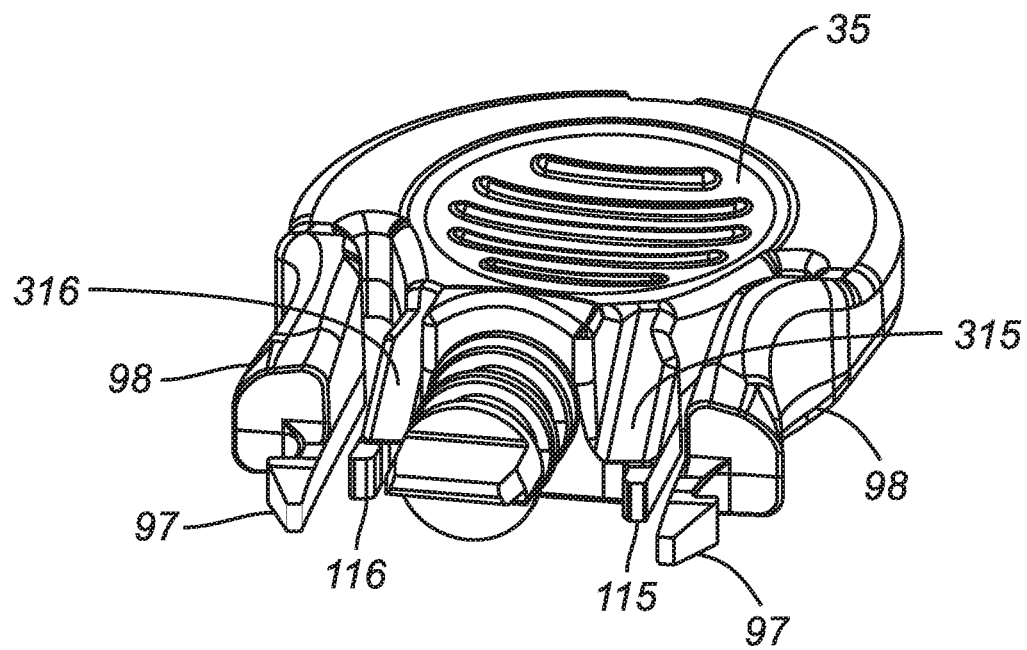
FIG. 36 illustrates a perspective view of a test plug.

In FIG. 36, however, the central section of the test plug or mounting base (not shown) includes anti-rotation arm extensions 315, 316 between the central section 35 and the anti-rotation arms 115, 116. The anti-rotation arm extensions 315, 316 may slope from the top of the central section 35 down toward the anti-rotation arms. By including anti-rotation arm extensions, especially those that slope down to the anti-rotation arms, it is possible to save materials when forming the test plug or mounting base. The extensions further allow the pockets to be cleaned while the test plug is connected. The extensions allow for a more consistent cross sectional thickness, which allows for faster times during molding and fewer cosmetic errors due to the effects of material shrinkage.

Any of the particular features discussed herein that may be used to lock-out non-compatible components may be used alone or in combination with each other, creating many possible iterations of connection configurations. Thus, it will be possible to ensure that many variations of components that are not compatible will not be able to connect to each other.

The sensor set of the present invention is mounted on the patient's skin quickly and easily to transcutaneously place the sensor 12. In one method, using the sensor in FIG. 4, for example, the mounting base 20 and connector 20 are initially coupled together by engaging the snap fit latch members. The hub 80 is also initially attached. The set is then pressed against the patient's skin, typically after removing a protective needle guard (not shown) and a release film (also not shown) from the underside of the adhesive patch 34 to expose a pressure sensitive adhesive thereon. Pressing the set against the skin causes the insertion needle 14 to pierce the skin and thereby carry the cannula 58 with the sensor electrodes 15 thereon to the desired subcutaneous position. The insertion needle 14 is then slidably disengaged from the cannula and sensor by withdrawing the needle from the patient. The insertion set 10 can be affixed more securely to the patient, if desired, by an overdressing (not shown). Alternatively, the mounting base may be affixed to the patient's skin before connecting to the connector. Thus, the connector would be connected to the mounting base after the mounting base is comfortably attached to the skin of the patient. It is also possible to disconnect the connector when the patient wishes to shower or wash the components. At this point, a dummy socket (not shown) can be connected to the mounting base to protect the electronic components inside the sensor.

When it is necessary or desirable to remove the sensor from the patient, the insertion set is simply removed from the patient's skin to withdraw the sensor from the subcutaneous site. The insertion set 10 is quickly and easily disassembled from the cable connector 20 by appropriate release of the snap fit latch members. A new insertion set 10 can then assembled with the cable connector and quickly placed on the patient to subcutaneously position a new sensor.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A sensor set for sensing a characteristic of a patient, the sensor set comprising:
    a sensor having at least two sensor electrodes thereon at a distal end for generating at least one electrical signal representative of a characteristic of a patient, the sensor including at least two contact pads at a proximal end, wherein each of the at least two contact pads are conductively coupled to at least one of the at least two sensor electrodes;
    a mounting base adapted to mount onto a patient's skin, the mounting base including a connector fitting generally at a rear end of the mounting base, wherein the connector fitting includes a cylindrical element having a central bore formed therein for pass through reception of a portion of the sensor,
    a connector adapted to couple to the mounting base and to connect the sensor to sensor electronics, wherein the connector includes a cylindrical recess sized to receive the connector fitting of the mounting base and at least two connector contacts that are adapted to be electrically coupled to the at least two contact pads of the sensor when the mounting base is coupled to the connector, wherein the connector fitting includes a key formed at one end, said key having a face at a proximal end adapted to be inserted into the connector, wherein the proximal end of the sensor folds around the face of the proximal end of the key such that at least one of the at least two contact pads is on a first side of the key and at least another of the at least two contact pads is on the second side of the key, and wherein the first side of the key and the second side of the key each include a substantially flat seat to receive the proximal end of the sensor, and further wherein the at least one of the at least two contact pads on the first side of the key is conductively coupled around the face of the proximal end of the key onto the second side of the key and to the at least one of the at least two sensor electrodes, and
    wherein the mounting base includes one or more latch arms and the connector includes one or more latch recesses, and wherein the one or more latch arms are adapted to fit and lock into the one or more latch recesses when the mounting base is coupled to the connector, and wherein the mounting base further includes one or more anti-rotation arms and the connector includes one or more anti-rotation arm recesses, wherein the one or more anti-rotation arms are adapted to fit into the one or more anti-rotation arm recesses when the mounting base is coupled to the connector.

2. The sensor set of claim 1, wherein the mounting base further includes one or more lockout pillars extending in the same direction as the one or more latch recesses and the connector includes one or more lockout pockets adapted to fit the lockout pillars, wherein when the mounting base is coupled to the connector.

3. The sensor set of claim 1, wherein the anti-rotation arms are wider than their height.

4. The sensor set of claim 1, wherein the one or more latch recesses are the same as the one or more anti-rotation arm recesses, such that the one or more latches fit into the same recesses as the one or more anti-rotation arms.

5. The sensor set of claim 1, further including a test plug adapted to connect to the connector, wherein the test plug includes one or more test plug latch arms adapted to fit and lock into the one or more latch recesses of the connector when the test plug is coupled to the connector, and wherein the test plug further includes one or more test plug anti-rotation arms adapted to fit into the one or more anti-rotation arm recesses of the connector when the test plug is coupled to the connector.

6. The sensor set of claim 5, wherein the test plug further includes one or more anti-rotation arm extensions between a central section of the test plug and the anti-rotation arms, wherein the anti-rotation arm extensions slope from the top of the central section to the anti-rotation arm extensions.

7. The sensor set of claim 5, wherein the test plug further includes one or more test plug lockout pillars extending in the same direction as the one or more test plug latch recesses adapted to fit into the lockout pockets of the connector when the test plug is coupled to the connector.

8. The sensor set of claim 1, wherein the key includes at least one prong adapted to fit into a prong recess formed in the mounting base.

9. The sensor set of claim 1, wherein the at least two connector contacts of the connector are compressible pins.

10. The sensor set of claim 9, wherein the compressible pins compress into the first side of the key and the second side of the key when the mounting base is coupled to the connector.

11. The sensor set of claim 1, wherein the sensor includes a shorting path for a shorted reference and counter electrode.

12. The sensor set of claim 1, wherein the sensor includes a resistor.

13. The sensor set of claim 1, wherein the connector includes a wireless transmitter adapted to transmit signals from the mounting base.

14. The sensor set of claim 1, wherein the characteristic is blood glucose.

15. The sensor set of claim 1, wherein the at least two sensor electrodes are adapted to generate at least two electrical signals representative of the characteristic and the at least two connector contacts are adapted to receive the at least two electrical signals.

16. The sensor set of claim 1, wherein the first side of the key includes a shelf portion and the mounting base includes a matching recess, whereby the shelf portion fits into the matching recess when the connector is connected to the mounting base.

17. A mounting base for a sensor, the mounting base comprising:
    a connector fitting generally at a rear end of the mounting base, wherein the connector fitting includes a cylindrical element having a central bore formed therein for pass through reception of a portion of a sensor wherein the sensor has at least two sensor electrodes thereon at a distal end for generating at least one electrical signal representative of a characteristic of a patient, the sensor including at least two contact pads at a proximal end, wherein each of the at least two contact pads are conductively coupled to at least one of the at least two sensor electrodes, wherein the connector fitting includes a key formed at one end, said key having a face at a proximal end adapted to be inserted into the connector, wherein the proximal end of the sensor folds around the face of the proximal end of the key such that at least one of the at least two contact pads is on a first side of the key and at least another of the at least two contact pads is on the second side of the key, and further wherein the at least one of the at least two contact pads on the first side of the key is conductively coupled around the face of the proximal end of the key onto the second side of the key and to the at least one of the at least two sensor electrodes;

one or more latch arms adapted to fit and lock into one or more latch recesses on a connector, wherein the connector is adapted to couple to the mounting base and to connect the sensor to sensor electronics and includes a cylindrical recess sized to receive the connector fitting of the mounting base and at least two connector contacts that are adapted to be electrically coupled to the at least two contact pads of the sensor when the mounting base is coupled to the connector; and one or more anti-rotation arms adapted to fit into one more anti-rotation recesses on the connector when the mounting base is coupled to the connector.

18. The mounting base of claim 17, wherein the anti-rotation arms are wider than they are in height.

* * * * *